United States Patent
Kandimalla et al.

(10) Patent No.: US 7,569,554 B2
(45) Date of Patent: *Aug. 4, 2009

(54) SYNERGISTIC TREATMENT OF CANCER USING IMMUNOMERS IN CONJUNCTION WITH THERAPEUTIC AGENTS

(75) Inventors: Ekambar R. Kandimalla, Southboro, MA (US); Sudhir Agrawal, Shrewsbury, MA (US); Daqing Wang, Bedford, MA (US); Lakshmi Bhagat, Framingham, MA (US); Dong Yu, Westboro, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 722 days.

This patent is subject to a terminal disclaimer.

(21) Appl. No.: 10/846,167

(22) Filed: May 14, 2004

(65) Prior Publication Data

US 2005/0009773 A1    Jan. 13, 2005

Related U.S. Application Data

(60) Provisional application No. 60/471,247, filed on May 16, 2003.

(51) Int. Cl.
- *A61K 39/395* (2006.01)
- *A61K 31/7105* (2006.01)
- *A61K 31/7115* (2006.01)
- *A61K 31/7125* (2006.01)

(52) U.S. Cl. .................... 514/44; 424/130.1; 424/156.1
(58) Field of Classification Search ................... 514/44; 424/130.1, 156.1
See application file for complete search history.

(56) References Cited

U.S. PATENT DOCUMENTS

| | | | |
|---|---|---|---|
| 5,366,878 A | 11/1994 | Pedersen et al. | |
| 5,635,377 A | 6/1997 | Pedersen et al. | |
| 5,652,355 A | 7/1997 | Metelev et al. | |
| 5,912,332 A | 6/1999 | Agrawal et al. | |
| 6,143,881 A | 11/2000 | Metelev et al. | |
| 6,346,614 B1 | 2/2002 | Metelev et al. | |
| 6,406,705 B1 | 6/2002 | Davis et al. | |
| 6,426,334 B1 | 7/2002 | Agrawal et al. | |
| 7,276,489 B2 * | 10/2007 | Agrawal et al. | 514/44 |
| 2001/0034330 A1 | 10/2001 | Kensil | |
| 2002/0132995 A1 | 9/2002 | Agrawal et al. | |

FOREIGN PATENT DOCUMENTS

| | | |
|---|---|---|
| WO | WO98/49288 | 11/1998 |
| WO | WO01/12804 | 2/2001 |
| WO | WO 01/83503 | 4/2001 |
| WO | WO 02/026757 | 7/2001 |
| WO | WO01/55370 | 8/2001 |
| WO | WO 0197843 A2 * | 12/2001 |
| WO | WO 0226757 A2 * | 4/2002 |
| WO | WO 03/035836 A2 | 5/2003 |
| WO | WO 03035836 A2 * | 5/2003 |

OTHER PUBLICATIONS

Kandimalla et al Bioconjugate Chem., 2002; 13: 966-974.*
Kandimalla et al, PNAS, 2003; 100: 14303-14308.*
Donnelly et al (Nature Medicine, 2003, 9/11:1354-1356).*
DeGruijl et al, Nature Medicine, 1999, 5/10:1124-1125.*
Bitton R. J. (Current Opinion in Molecular Therapeutics, 2004, 6/1:17-25).*
Weiner J. Leukocyte Biology, 2000; 68: 455-463.*
Krieg et al Nature 374:546-549 (1995).*
Ballas et al J. Immunology 2001; 167: 4878.*
Agrawal et al (Trends in Molecular Medicine, 2002, 8/3:114-120).*
Wiesenthal (http://weisenthal.org/feedback. html, Feb. 4, 2002).*
Tallarida (Drug Synergism and Dose-effect Analysis, Chapman & Hall/CRC, Boca Raton, 2000, pp. 1-13).*
Berenbaum ("Synergy, additivism and antagonism in immunosuppression," Clin exp Immunol 28:1-18, 1977).*
Wooldrige et al. (Blood 1997; 89: 2994-2998).*
Herceptin® Package Insert (Dec. 11, 2001).*
Kuramoto et al. (1992) Jpn. J. Cancer Res. 83:1128-1131.
Krieg et al. (1995) Nature 374: 546-549.
Liang et al. (1996) J. Clin. Invest. 98: 1119-1129.
Zhao et al. (1996) Biochem. Pharmacol. 51:173-182.
Zhao et al. (1996) Biochem. Pharmacol. 52:1537-1544.
Zhao et al. (1997) Antisense Nucleic Acid Drug Dev. &:495-502.
McCluskie et al. (1998) J. Immunol. 161:4463-4466.
Moldoveanu et al. (1998) Vaccine 16:1216-124.
Zhao et al. (1999) Bioorg. Med. Chem. Lett. 9:3453-3458.
Zhao et al. (2000) Bioorg. Med. Chem. Lett. 19:1051-1054.
Yu et al. (2000) Bioorg. Med. Chem. Lett. 10:2585-2588.
Kandimalla et al. (2001) Bioorg. Med. Chem. 9:807-813.
Yu et al. (2001) Bioorg. Med. Chem. Lett. 11:2263-2267.
Warren et al., "Synergism Between Cytosine-Guanine Oligodeoxynucleotides and Monoclonal Antibody in the Treatment of Lymphoma", Seminars in. Oncol. 2002, vol. 29(1)(2). pp. 93-97.
Cheng et al., "Inhibition of DNA Methylation and Reactivation of Silenced Genes by Zebularine", J. Nat. Cancer Inst. 2003, vol. 95(5), pp. 399-409.
Weigel et al., "CpG Oligodeoxynucleotides Potentiate the Antitumor Effects of Chemotherapy or Tumor Resection in an Orthotopic Mutine Model of Rhabdomyosarcoma", Clin. Cancer Resear. 2003, vol. 9, pp. 3105-3114.
Kandimalla et al., "A Dinucleotide Motif in Oligonucleotides Shows Potent Immunomodulatory Activity and Overrides Species-Specific Recognition Observed with CpG Motif", PNAS 2003, vol. 100(24), pp. 14303-14308.

* cited by examiner

*Primary Examiner*—Brandon J Fetterolf
(74) *Attorney, Agent, or Firm*—Wayne A. Keown; Joseph C. Zucchero; Keown & Zucchero, LLP

(57) ABSTRACT

The invention relates to the therapeutic use of immunostimulatory oligonucleotides and/or immunomers in combination with chemotherapeutic agents to provide a synergistic therapeutic effect.

2 Claims, 30 Drawing Sheets

Linkers for linear synthesis

Linear Synthesis of Immunomers

Parallel Synthesis of Immunomers

Figure 15

| Number | Structure[a] | Motif | Modification |
|---|---|---|---|
| IMO 1 | 5'-TCTGACGTTCT-X-TCTTGCAGTCT-5' | Mouse | Natural CpG |
| IMO 2 | 5'-TCTGACRTTCT-X-TCTTRCAGTCT-5' | Mouse | Synthetic CpR |
| IMO 3 | 5'-TCTGTCRTTCT-X-TCTTRCTGTCT-5' | Human | Synthetic CpR |

[a]: X and R are glycerol linker and 2'-deoxy-7-deazaguanosine, respectively.

SYNERGISTIC TREATMENT OF CANCER USING IMMUNOMERS IN CONJUNCTION WITH THERAPEUTIC AGENTS

RELATED APPLICATION

This application claims the benefit of U.S. Provisional Application No. 60/471,247, filed May 16, 2003, which is incorporated by reference in its entirety.

BACKGROUND OF THE INVENTION

1. Field of the Invention

The invention relates to anti-cancer applications using immunomers as therapeutic agents.

2. Summary of the Related Art

Recently, several researchers have demonstrated the validity of the use of oligonucleotides as immunostimulatory agents in immunotherapy applications. The observation that phosphodiester and phosphorothioate oligonucleotides can induce immune stimulation has created interest in developing these compounds as a therapeutic tool. These efforts have focused on phosphorothioate oligonucleotides containing the natural dinucleotide CpG. Kuramoto et al., *Jpn. J. Cancer Res.* 83:1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371:546-549 (1995) discloses that phosphorothioate CpG-containing oligonucleotides are immunostimulatory. Liang et al., *J. Clin. Invest.* 98:1119-1129 (1996) discloses that such oligonucleotides activate human B cells. Moldoveanu et al., *Vaccine* 16:1216-124 (1998) teaches that CpG-containing phosphorothioate oligonucleotides enhance immune response against influenza virus. McCluskie and Davis, *J. Immunol.* 161:4463-4466 (1998) teaches that CpG-containing oligonucleotides act as potent adjuvants, enhancing immune response against hepatitis B surface antigen.

Other modifications of CpG-containing phosphorothioate oligonucleotides can also affect their ability to act as modulators of immune response. See, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med. Chem. Lett.* (1999) 9:3453-3458; Zhao et al., *Bioorg. Med. Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med. Chem.* (2001) 9:807-813. U.S. Pat. No. 6,426,334 shows the promise of these compounds as anti-cancer agents.

Although it has been well demonstrated that many murine and human tumors carry immunogenic epitopes that can be recognized by the host immune system, in most cases host defenses fail to mount an appropriate response causing uncontrolled tumor growth in cancer patients. The failure of the host immune system to elicit defense against tumor cells could be related to low immunogenic nature of tumor antigens and/or defects in the host immune system itself.

These reports make clear that there remains a need to be able to enhance the anticancer activity of immunostimulatory oligonucleotides.

BRIEF SUMMARY OF THE INVENTION

The invention provides methods for enhancing the anti-cancer activity of immunostimulatory oligonucleotide compounds. The methods according to the invention enable synergy between the immunostimulatory effect of immunostimulatory oligonucleotides and the therapeutic effect of chemotherapeutic agents. Modification of an immunostimulatory oligonucleotide to optimally present 5' ends dramatically enhances its anti-cancer activity. Such an oligonucleotide is referred to herein as an "immunomer", which may contain one or more immunostimulatory oligonucleotide.

In a first aspect, therefore, the invention provides methods for treating cancer in a cancer patient comprising administering to the patient an immunostimulatory oligonucleotide and/or immunomer in combination with a chemotherapeutic agent, wherein the immunostimulatory oligonucleotide and/or immunomer and the chemotherapeutic agent create a synergistic therapeutic effect.

In some embodiments, the immunostimulatory oligonucleotide and/or immunomer used in the method according to the invention comprises an immunostimulatory dinucleotide selected from the group consisting of CpG, C*pG, CpG*, and C*pG*, wherein C is cytidine or 2'-deoxycytidine, C* is 2'-deoxythymidine. arabinocytidine, 2'-deoxy-2'-substituted arabinocytidine, 2'-O-substitutedarabinocytidine, 2'-deoxy-5-hydroxycytidine, 2'-deoxy-N-4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine; G is guanosine or 2'-deoxyguanosine, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

In some embodiments, the immunostimulatory oligonucleotide and/or immunomer used in the method according to the invention comprises an immunostimulatory domain of formula (III):

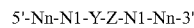

5'-Nn-N1-Y-Z-N1-Nn-3'     (III)

wherein:

Y is cytidine, 2'-deoxythymidine, 2'-deoxycytidine, arabinocytidine, 2'-deoxy-2'-substitutedarabinocytidine, 2'-O-substitutedarabinocytidine, 2'-deoxy-5-hydroxycytidine, 2'-deoxy-N-4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine;

Z is guanosine or 2'-deoxyguanosine, is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside N1, at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

Nn, at each occurrence, is a naturally occurring nucleoside or an immunostimulatory moiety, preferably selected from the group consisting of abasic nucleosides, arabinonucleosides, 2'-deoxyuridine, α-deoxyribonucleosides, 2'-O-substituted ribonucleosides, and nucleosides linked by a modified internucleoside linkage to the adjacent nucleoside on the 3' side, the modified internucleotide linkage being selected from the group consisting of amino linker, C2-C18 alkyl linker, poly(ethylene glycol) linker, 2-aminobutyl-1,3-propanediol linker, glyceryl linker, 2'-5' internucleoside linkage, and methylphosphonate internucleoside linkage;

provided that at least one N1 or Nn is an immunostimulatory moiety;

wherein n is a number from 0-30;

wherein the 3'nucleoside is optionally linked directly or via a non-nucleotidic linker to another oligonucleotide, which may or may not be immunostimulatory.

In a second aspect, the invention provides a method for treating cancer in a cancer patient comprising administering an immunostimulatory oligonucleotide and/or immunomer conjugate, which comprises an immunostimulatory oligonucleotide and/or immunomer, as described above, and a cancer antigen conjugated to the immunostimulatory oligonucleotide and/or immunomer at a position other than the accessible 5' end, in combination with a chemotherapeutic agent.

In a third aspect, the invention provides pharmaceutical formulations comprising an immunostimulatory oligonucleotide and/or immunostimulatory oligonucleotide and/or an immunomer or immunomer conjugate according to the invention, a chemotherapeutic agent and a physiologically acceptable carrier.

BRIEF DESCRIPTION OF THE DRAWINGS

FIG. 15 shows examples of IMO compound structures and modifications (SEQ ID NOS 13, 24, and 18, respectively in order of appearance ).

DETAILED DESCRIPTION OF THE PREFERRED EMBODIMENTS

Figure 1:
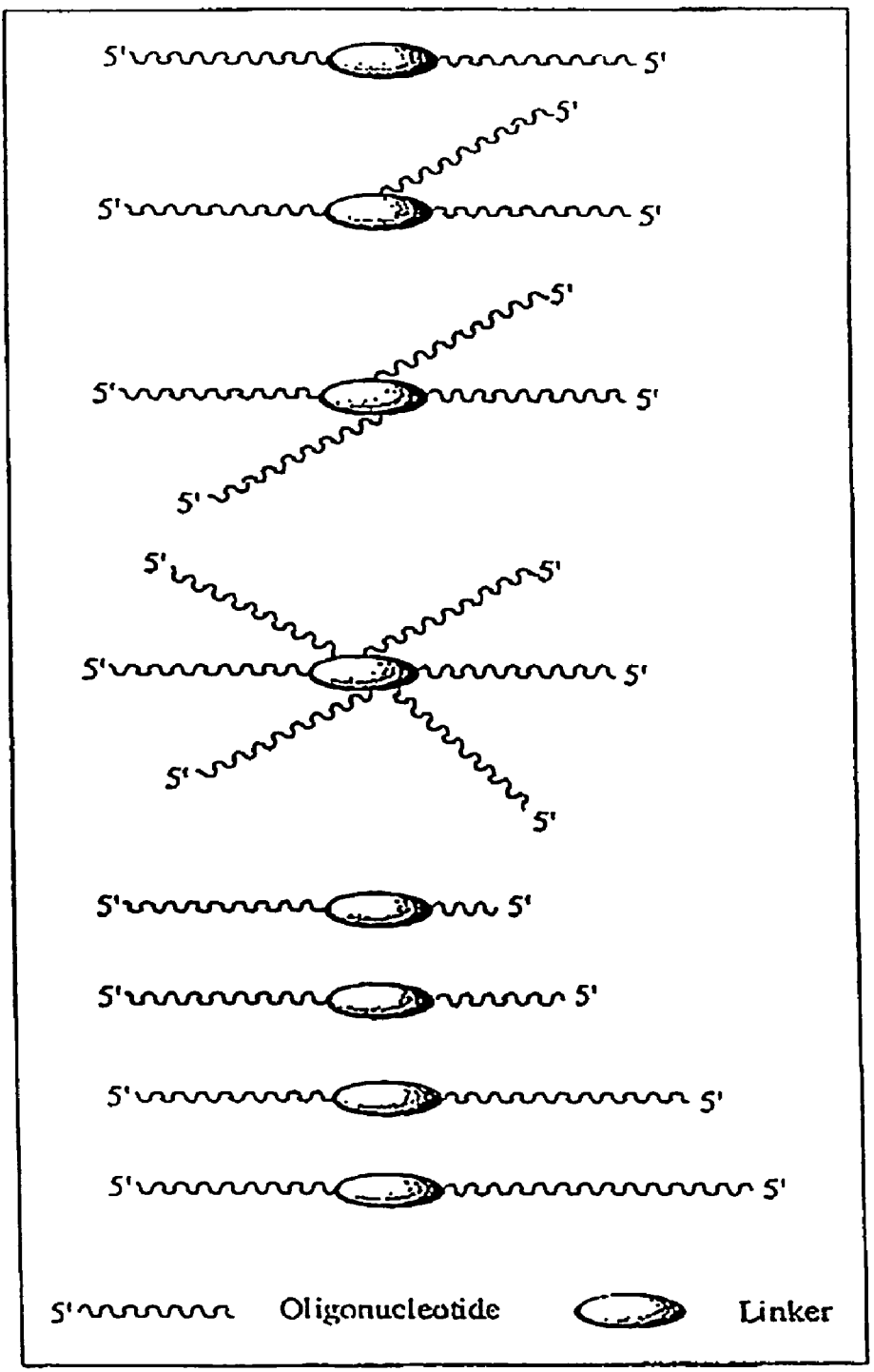
FIG. 1 is a schematic representation of representative immunomers of the invention.
Figure 2:
FIG. 2 (all oligonucleotides shown are disclosed as SEQ ID NO: 2) depicts several representative immunomers of the invention.
Figure 3:
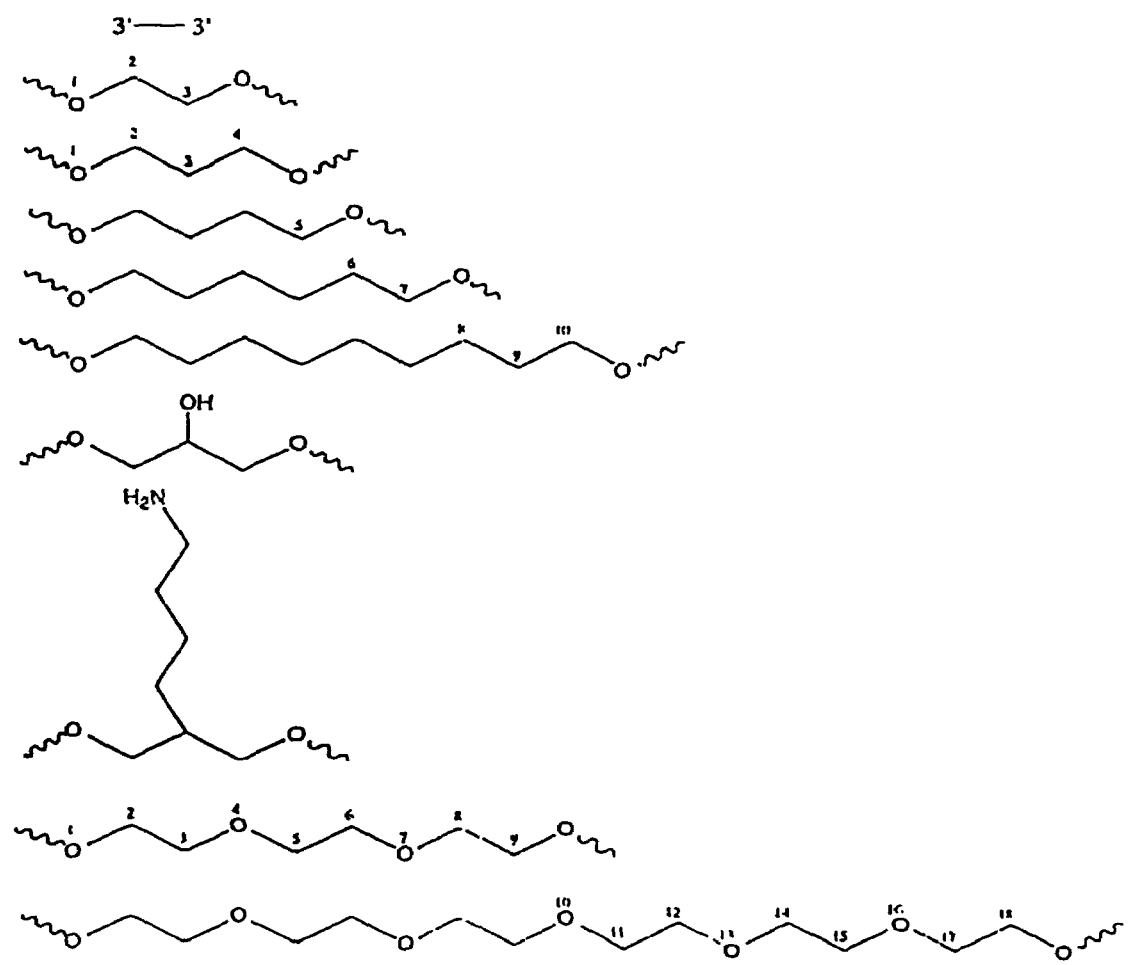
FIG. 3 depicts a group of representative small molecule linkers suitable for linear synthesis of immunomers of the invention.
Figure 4:
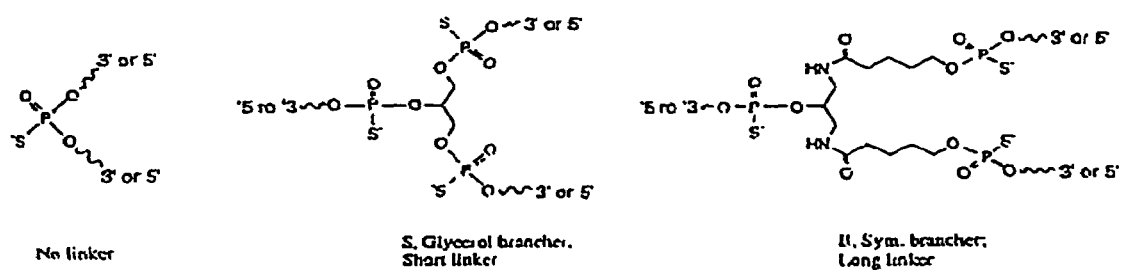
FIG. 4 depicts a group of representative small molecule linkers suitable for parallel synthesis of immunomers of the invention.

The invention relates to the therapeutic use of immunostimulatory oligonucleotides and/or immunomers as anticancer agents in combination with chemotherapeutic agents. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing the anticancer effect caused by immunostimulatory compounds used for immunotherapy applications for the treatment of cancer. The immunomers and/or immunostimulatory oligonucleotides of the invention can be used to treat, prevent or ameliorate the onset and/or progression of a tumor or cancer (e.g., tumors of the brain, lung (e.g., small cell and non-small cell), ovary, breast, prostate, colon, glioma, as well as other melanoma, carcinomas, leukemias, lymphomas and sarcomas). In the methods according to the invention, immunostimulatory oligonucleotides and/or immunomers provide a synergistic therapeutic effect when use in combination with chemotherapeutic agents. This result is surprising in view of the fact that immunostimulatory oligonucleotides and immunomers cause cell division of immune system cells, whereas chemotherapeutic agents normally kill actively dividing cells.

In a first aspect, the invention provides a method for treating cancer in a cancer patient comprising administering, in combination with chemotherapeutic agents, immunostimulatory oligonucleotides and/or immunomers, the latter comprising at least two oligonucleotides linked together, such that the immunomer has more than one accessible 5' end, wherein at least one of the oligonucleotides is an immunostimulatory oligonucleotide. As used herein, the term "accessible 5'end" means that the 5' end of the oligonucleotide is sufficiently available such that the factors that recognize and bind to immunomers and stimulate the immune system have access to it. Optionally, the 5' OH can be linked to a phosphate, phosphorothioate, or phosphorodithioate moiety, an aromatic or aliphatic linker, cholesterol, or another entity which does not interfere with accessibility. Immunostimulatory oligonucleotides and immunomers induce an immune response when administered to a vertebrate. When used in combination with chemotherapeutic agents, a synergistic therapeutic effect is obtained.

Preferred chemotherapeutic agents used in the method according to the invention include, without limitation Gemcitabine, methotrexate, vincristine, adriamycin, cisplatin, non-sugar containing chloroethylnitrosoureas, 5-fluorouracil, mitomycin C, bleomycin, doxorubicin, dacarbazine, Taxol®, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin®/Topotecan, PKC412, Valspodar®/PSC833, Novantrone®/Mitroxantrone, Metaret/Suramin, Batimastat, E7070, BCH-4556, CS-682, 9-AC, AG3340, AG3433, InceVVX-710, VX-853, ZD0101, ISI641, ODN 698, TA 2516/Marmistat, BB2516/Marmistat, CDP 845, D2163, PD183805, DX8951f, Lemonal DP 2202, FK 317, imatinib mesylate/Gleevec®, Picibani/OK-432, AD 32/Valrubicin, Metastron®/strontium derivative, Temodal/Temozolomide, Evacet/liposomal doxorubicin, Yewtaxan/Placlitaxel, Taxol®/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT™(Tegafur/Uracil), Ergamisol®/Levamisole, Eniluracil/776C85/5FU enhancer, Campto/Levamisole, Camptosar®/Irinotecan, Tumodex/Ralitrexed, Leustatin/Cladribine, Paxex/Paclitaxel, Doxil®/liposomal doxorubicin, Caelyx/liposomal doxorubicin, Fludara®/Fludarabine, Pharmarubicin/Epirubicin, DepoCyt®, ZD1839, LU 79553/Bis-Naphtalimide, LU 103793/Dolastain, Caetyx/liposomal doxorubicin, Gemzar®/Gemcitabine, ZD 0473/Anormed®, YM 116, Iodine seeds, CDK4 and CDK2 inhibitors, PARP inhibitors, D4809/Dexifosamide, Ifes/Mesnex®/Ifosamide, Vumon®/Teniposide, Paraplatin®/Carboplatin, Plantinol/cisplatin, Vepeside/Etoposide, ZD 9331, Taxotere®/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In the methods according to this aspect of the invention, administration of immunostimulatory oligonucleotides and/or immunomers can be by any suitable route, including, without limitation, parenteral, oral, sublingual, transdermal, topical, intranasal, aerosol, intraocular, intratracheal, intrarectal, vaginal, by gene gun, dermal patch or in eye drop or mouthwash form. Administration of the therapeutic compositions of immunostimulatory oligonucleotides and/or immunomers can be carried out using known procedures at dosages and for periods of time effective to reduce symptoms or surrogate markers of the disease. When administered systemically, the therapeutic composition is preferably administered at a sufficient dosage to attain a blood level of immunostimulatory oligonucleotide and/or immunomer from about 0.0001 micromolar to about 10 micromolar. For localized administration, much lower concentrations than this may be effective, and much higher concentrations may be tolerated. Preferably, a total dosage of immunostimulatory oligonucleotide and/or immunomer ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

For purposes of this aspect of the invention, the term "in combination with" means in the course of treating the same disease in the same patient, and includes administering the immunostimulatory oligonucleotide and/or immunomer and/or the chemotherapeutic agent in any order, including simultaneous administration, as well as temporally spaced order of up to several days apart. Such combination treatment may also include more than a single administration of the immunostimulatory oligonucleotide and/or immunomer, and/or independently the chemotherapeutic agent. The administration of the immunostimulatory oligonucleotide and/or immunomer and/or chemotherapeutic agent may be by the same or different routes.

In some embodiments, the immunomer used in the method according to the invention comprises two or more immunostimulatory oligonucleotides, (in the context of the immunomer) which may be the same or different. Preferably, each such immunostimulatory oligonucleotide has at least one accessible 5' end.

In certain embodiments of the method according to the invention, in addition to the immunostimulatory oligonucleotide(s), the immunomer also comprises at least one oligonucleotide that is complementary to a gene. As used herein, the term "complementary to" means that the oligonucleotide hybridizes under physiological conditions to a region of the gene. In some embodiments, the oligonucleotide downregulates expression of a gene. Such downregulatory oligonucleotides preferably are selected from the group consisting of antisense oligonucleotides, ribozyme oligonucleotides, small inhibitory RNAs and decoy oligonucleotides. As used herein, the term "downregulate a gene" means to inhibit the transcription of a gene or translation of a gene product. Thus, the immunomers used in the method according to the invention can be used to target one or more specific disease targets, while also stimulating the immune system.

In certain embodiments, the immunostimulatory oligonucleotide and/or immunomer used in the method according to the invention includes a ribozyme or a decoy oligonucleotide. As used herein, the term "ribozyme" refers to an oligonucleotide that possesses catalytic activity. Preferably, the ribozyme binds to a specific nucleic acid target and cleaves the target. As used herein, the term "decoy oligonucleotide" refers to an oligonucleotide that binds to a transcription factor in a sequence-specific manner and arrests transcription activity. Preferably, the ribozyme or decoy oligonucleotide exhibits secondary structure, including, without limitation, stem-loop or hairpin structures. In certain embodiments, at least one oligonucleotide comprises poly(I)-poly(dC). In certain embodiments, at least one set of Nn includes a string of 3 to 10 dGs and/or Gs or 2'-substituted ribo or arabino Gs.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide"

are expressly intended to include polynucleosides and dinucleosides having any such internucleoside linkage, whether or not the linkage comprises a phosphate group. In certain preferred embodiments, these internucleoside linkages may be phosphodiester, phosphorothioate, phosphorodithioate, methylphosphonate linkages, or combinations thereof.

In some embodiments, the immunomer comprises oligonucleotides each having from about 3 to about 35 nucleoside residues, preferably from about 4 to about 30 nucleoside residues, more preferably from about 4 to about 20 nucleoside residues. In some embodiments, the oligonucleotides have from about 5 or 6 to about 18, or from about 5 or 6 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above, for purposes of this invention. In some embodiments, one or more of the oligonucleotides have 11 nucleotides.

The term "Oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The immunostimulatory oligonucleotides and/or immunomers used in the method according to the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-fluoroarabinoside.

For purposes of the invention, the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of such 2'-O-substituted ribonucleosides include, without limitation 2'-O-methylribonucleosides and 2'-O-methoxyethylribonucleosides.

The term "2'-substituted ribonucleoside" also includes ribonucleosides in which the 2'-hydroxyl group is replaced with a lower alkyl group containing 1-6 saturated or unsaturated carbon atoms, or with an amino or halo group. Examples of such 2'-substituted ribonucleosides include, without limitation, 2'-amino, 2'-fluoro, 2'-allyl, and 2'-propargyl ribonucleosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

For purposes of the invention, the term "immunostimulatory oligonucleotide" refers to an oligonucleotide as described above that induces an immune response when administered to a vertebrate, such as a fish, bird, or mammal. As used herein, the term "mammal" includes, without limitation rats, mice, cats, dogs, horses, cattle, cows, pigs, rabbits, non-human primates, and humans. Useful immunostimulatory oligonucleotides can be found described in Agrawal et al., WO 98/49288, published Nov. 5, 1998; WO 01/12804, published Feb. 22, 2001; WO 01/55370, published Aug. 2, 2001; PCT/US01/13682, filed Apr. 30, 2001; and PCT/US01/30137, filed Sep. 26, 2001. Preferably, the immunostimulatory oligonucleotide comprises at least one phosphodiester, phosphorothioate, methylphosphonate, or phosphordithioate internucleoside linkage.

In some embodiments, at least one immunostimulatory oligonucleotide of the immunomer comprises an immunostimulatory dinucleotide of formula 5'-Pyr-Pur-3', wherein Pyr is a natural or synthetic pyrimidine nucleoside and Pur is a natural or synthetic purine nucleoside. As used herein, the term "pyrimidine nucleoside" refers to a nucleoside wherein the base component of the nucleoside is a pyrimidine base. Similarly, the term "purine nucleoside" refers to a nucleoside wherein the base component of the nucleoside is a purine base. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides in the immunostimulatory oligonucleotides and/or immunomers used in the method according to the invention have the structure (I):

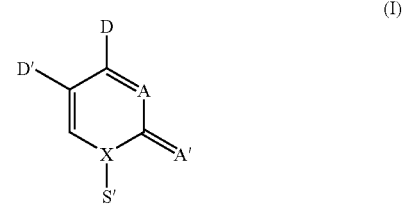

(i) wherein:

D is a hydrogen bond donor;

D' is selected from the group consisting of hydrogen, hydrogen bond donor, hydrogen bond acceptor, hydrophilic group, hydrophobic group, electron withdrawing group and electron donating group;

A is a hydrogen bond acceptor or a hydrophilic group;

A' is selected from the group consisting of hydrogen bond acceptor, hydrophilic group, hydrophobic group, electron withdrawing group and electron donating group;

X is carbon or nitrogen; and

S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of preferred sugar moieties.

Preferred purine nucleoside analogs in immunostimulatory oligonucleotides and/or immunomers used in the method according to the invention have the structure (II):

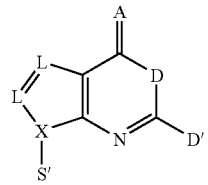

(II)

(ii) wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH$_2$, —SH and —OH. Preferred hydrogen bond acceptors include, without limitation, C=O, C=S, —NO$_2$ and the ring nitrogen atoms of an aromatic heterocycle, e.g., N1 of guanine.

In some embodiments, the base moiety in (II) is a non-naturally occurring purine base. Examples of preferred non-naturally occurring purine bases include, without limitation, 6-thioguanine and 7-deazaguanine. In some embodiments, the sugar moiety S' in (II) is a naturally occurring sugar moiety, as described above for structure (I).

In preferred embodiments, the immunostimulatory dinucleotide in the immunostimulatory oligonucleotides and/or immunomer used in the method according to the invention is selected from the group consisting of CpG, C*pG, CpG*, and C*pG*, wherein C is cytidine or 2'-deoxycytidine, C* is 2'-deoxythymidine, arabinocytidine, 2'-deoxythymidine, 2'-deoxy-2'-substitutedarabinocytidine, 2'-O-substitutedarabinocytidine, 2'-deoxy-5-hydroxycytidine, 2'-deoxy-N-4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine; G is guanosine or 2'-deoxyguanosine, G* is 2' deoxy-7-deazaguanosine, 2'-deoxy-6-thioguanosine, arabinoguanosine, 2'-deoxy-2' substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

The immunostimulatory oligonucleotides may include immunostimulatory moieties on one or both sides of the immunostimulatory dinucleotide. Thus, in some embodiments, the immunostimulatory oligonucleotide comprises an immunostimulatory domain of structure (III):

$$5'\text{-Nn-N1-Y-Z-N1-Nn-}3' \quad (III)$$

wherein:

Y is cytidine, 2'deoxythymidine, 2' deoxycytidine arabinocytidine, 2'-deoxy-2'-substitutedarabinocytidine, 2'-deoxythymidine, 2'-O-substitutedarabinocytidine, 2'-deoxy-5-hydroxycytidine, 2'-deoxy-N-4-alkyl-cytidine, 2'-deoxy-4-thiouridine, other non-natural pyrimidine nucleosides, orl-(2'-deoxy-β-D-ribofuranosyl)-2-oxo-7-deaza-8-methyl-purine;

Z is guanosine or 2'-deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'deoxyinosine, or other non-natural purine nucleoside;

N1, at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

Nn, at each occurrence, is preferably a naturally occurring nucleoside or an immunostimulatory moiety selected from the group consisting of abasic nucleosides, arabinonucleosides, 2'-deoxyuridine, α-deoxyribonucleosides, 2'-O-substituted ribonucleosides, and nucleosides linked by a modified internucleoside linkage to the adjacent nucleoside on the 3' side, the modified internucleoside linkage preferably being selected from the group consisting of amino linker, C2-C$_{1-8}$ alkyl linker, poly(ethylene glycol) linker, 2-aminobutyl-1,3-propanediol linker, glyceryl linker, 2'-5' internucleoside linkage, and methylphosphonate internucleoside linkage;

provided that at least one N1 or Nn is an immunostimulatory moiety;

wherein each n is independently a number from 0 to 30; and wherein, in the case of an immunomer, the 3'end is linked directly or via a non-nucleotidic linker to another oligonucleotide, which may or may not be immunostimulatory.

In some preferred embodiments, YZ is arabinocytidine or 2'-deoxy-2'-substituted arabinocytidine and arabinoguanosine or 2'deoxy-2'-substituted arabinoguanosine. Preferred immunostimulatory moieties include modifications in the phosphate backbones, including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., $(R_P)$- or $(S_P)$-phosphorothioate, alkylphosphonate, or phosphotriester linkages).

Preferred immunostimulatory moieties according to the invention further include nucleosides having sugar modifications, including, without limitation, 2'-substituted pentose sugars including, without limitation, 2'-O-methylribose, 2'-O-methoxyethylribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethyl-arabinose, and 2'-substituted arabinose sugars; hexose sugars, including, without limitation, 1,5-anhydrohexitol; and alpha-anomers. In embodiments in which the modified sugar is a 3'-deoxyribonucleoside or a 3'-O-substituted ribonucleoside, the immunostimulatory moiety is attached to the adjacent nucleoside by way of a 2'-5' internucleoside linkage.

Preferred immunostimulatory moieties in immunostimulatory oligonucleotides and/or immunomers used in the method according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some such functionalized alkyl linkers are poly(ethylene glycol) linkers of formula —O—(CH$_2$—CH$_2$—O—)$_n$ (n=1-9). Some other functionalized alkyl linkers are peptides or amino acids.

Preferred immunostimulatory moieties in immunostimulatory oligonucleotides and/or immunomers used in the method according to the invention further include DNA isoforms, including, without limitation, β-L-deoxyribonucleosides and α-deoxyribonucleosides. Preferred immunostimulatory moieties incorporate 3' modifications, and further include nucleosides having unnatural internucleoside linkage positions, including, without limitation, 2'-5',2'-2',3'-3' and 5'-5' linkages.

Preferred immunostimulatory moieties in immunostimulatory oligonucleotides and/or immunomers used in the method according to the invention further include nucleosides having modified heterocyclic bases, including, without limitation, 5-hydroxycytosine, 5-hydroxymethylcytosine, N4-alkylcytosine, preferably N4-ethylcytosine, 4-thiouracil, 6-thioguanine, 7-deazaguanine, inosine, nitropyrrole, C5-propynylpyrimidine, and diaminopurines, including, without limitation, 2,6-diaminopurine.

By way of specific illustration and not by way of limitation, for example, in the immunostimulatory domain of structure (III), a methylphosphonate internucleoside linkage at position N1 or Nn is an immunostimulatory moiety, a linker having a length of from about 2 angstroms to about 200 angstroms, C2-C18 alkyl linker at position X1 is an immunostimulatory moiety, and a β-L-deoxyribonucleoside at position X1 is an immunostimulatory moiety. See Table 1 below for representative positions and structures of immunostimulatory moieties. It is to be understood that reference to a linker as the immunostimulatory moiety at a specified position means that the nucleoside residue at that position is substituted at its 3'-hydroxyl with the indicated linker, thereby creating a modified internucleoside linkage between that nucleoside residue and the adjacent nucleoside on the 3' side. Similarly, reference to a modified internucleoside linkage as the immunostimulatory moiety at a specified position means that the nucleoside residue at that position is linked to the adjacent nucleoside on the 3' side by way of the recited linkage.

TABLE 1

| Position | TYPICAL IMMUNOSTIMULATORY MOIETIES |
|---|---|
| N1 | Naturally-occurring nucleosides, abasic nucleoside, arabinonucleoside, 2'-deoxyuridine, β-L-deoxyribonucleoside C2-C18 alkyl linker, poly(ethylene glycol) linkage, 2-aminobutyl-1,3-propanediol linker (amino linker), 2'-5' internucleoside linkage, methylphosphonate internucleoside linkage |
| Nn | Naturally-occurring nucleosides, abasic nucleoside, arabinonucleosides, 2'-deoxyuridine, 2'-O-substituted ribonucleoside, 2'-5' internucleoside linkage, methylphosphonate internucleoside linkage, provided that N1 and N2 cannot both be abasic linkages |

Table 2 shows representative positions and structures of immunostimulatory moieties within an immunostimulatory oligonucleotide having an upstream potentiation domain. As used herein, the term "Spacer 9" refers to a poly(ethylene glycol) linker of formula —O—(CH$_2$CH$_2$—O)$_n$—, wherein n is 3. The term "Spacer 18" refers to a poly(ethylene glycol) linker of formula —O—(CH$_2$CH$_2$—O)$_n$—, wherein n is 6. As used herein, the term "C2-C18 alkyl linker refers to a linker of formula —O—(CH$_2$)$_q$—O—, where q is an integer from 2 to 18. Accordingly, the terms "C3-linker" and "C3-alkyl linker" refer to a linker of formula —O—(CH$_2$)$_3$—O—. For each of Spacer 9, Spacer 18, and C2-C18 alkyl linker, the linker is connected to the adjacent nucleosides by way of phosphodiester, phosphorothioate, phosphorodithioate or methylphosphonate linkages.

TABLE 2

| Position | TYPICAL IMMUNOSTIMULATORY MOIETY |
|---|---|
| 5' N2 | Naturally-occurring nucleosides, 2-aminobutyl-1,3-propanediol linker |
| 5' N1 | Naturally-occurring nucleosides, β-L-deoxyribonucleoside, C2-C18 alkyl linker, poly(ethylene glycol), abasic linker, 2-aminobutyl-1,3-propanediol linker |
| 3' N1 | Naturally-occurring nucleosides, 1',2'-dideoxyribose, 2'-O-methyl-ribonucleoside, C2-C18 alkyl linker, Spacer 9, Spacer 18 |

TABLE 2-continued

| Position | TYPICAL IMMUNOSTIMULATORY MOIETY |
|---|---|
| 3' N2 | Naturally-occurring nucleosides, 1',2'-dideoxyribose, 3'-deoxyribonucleoside, β-L-deoxyribonucleoside, 2'-O-propargyl-ribonucleoside, C2-C18 alkyl linker, Spacer 9, Spacer 18, methylphosphonate internucleoside linkage |
| 3' N3 | Naturally-occurring nucleosides, 1',2'-dideoxyribose, C2-C18 alkyl linker, Spacer 9, Spacer 18, methylphosphonate internucleoside linkage, 2'-5' internucleoside linkage, d(G)n, polyI-polydC |
| 3' N2 + 3' N3 | 1',2'-dideoxyribose, β-L-deoxyribonucleoside, C2-C18 alkyl linker, d(G)n, polyI-polydC |
| 3' N3 + 3' N4 | 2'-O-methoxyethyl-ribonucleoside, methylphosphonate internucleoside linkage, d(G)n, polyI-polydC |
| 3' N5 + 3' N6 | 1',2'-dideoxyribose, C2-C18 alkyl linker, d(G)n, polyI-polydC |
| 5' N1 + 3' N3 | 1',2'-dideoxyribose, d(G)n, polyI-polydC |

Table 3 shows representative positions and structures of immunostimulatory moieties within an immunostimulatory oligonucleotide having a downstream potentiation domain.

TABLE 3

| Position | TYPICAL IMMUNOSTIMULATORY MOIETY |
|---|---|
| 5' N2 | methylphosphonate internucleoside linkage |
| 5' N1 | methylphosphonate internucleoside linkage |
| 3' N1 | 1',2'-dideoxyribose, methylphosphonate internucleoside linkage, 2'-O-methyl |
| 3' N2 | 1',2'-dideoxyribose, β-L-deoxyribonucleoside, C2-C18 alkyl linker, Spacer 9, Spacer 18, 2-aminobutyl-1,3-propanediol linker, methylphosphonate internucleoside linkage, 2'-O-methyl |
| 3' N3 | 3'-deoxyribonucleoside, 3'-O-substituted ribonucleoside, 2'-O-propargyl-ribonucleoside |
| 3' N2 + 3' N3 | 1',2'-dideoxyribose, β-L-deoxyribonucleoside |

The immunomers used in the method according to the invention comprise at least two oligonucleotides linked directly or via a non-nucleotidic linker. For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides. For purposes of this invention, such a direct 3'-3' linkage is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

In yet other embodiments, the non-nucleotidic linker is an organic moiety having functional groups that permit attachment to the oligonucleotide. Such attachment preferably is by any stable covalent linkage.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotidic linkers in immunomers used in the method according to the invention permit attachment of more than two oligonucleotides, as schematically depicted in FIG. 1. For example, the small molecule linker glycerol has three hydroxyl groups to which oligonucleotides may be covalently attached. Some immunomers according to the invention, therefore, comprise more than two oligonucleotides linked at their 3' ends to a non-nucleotidic linker. Some such immunomers comprise at least two immunostimulatory oligonucleotides, each having an accessible 5' end.

Figure 5:
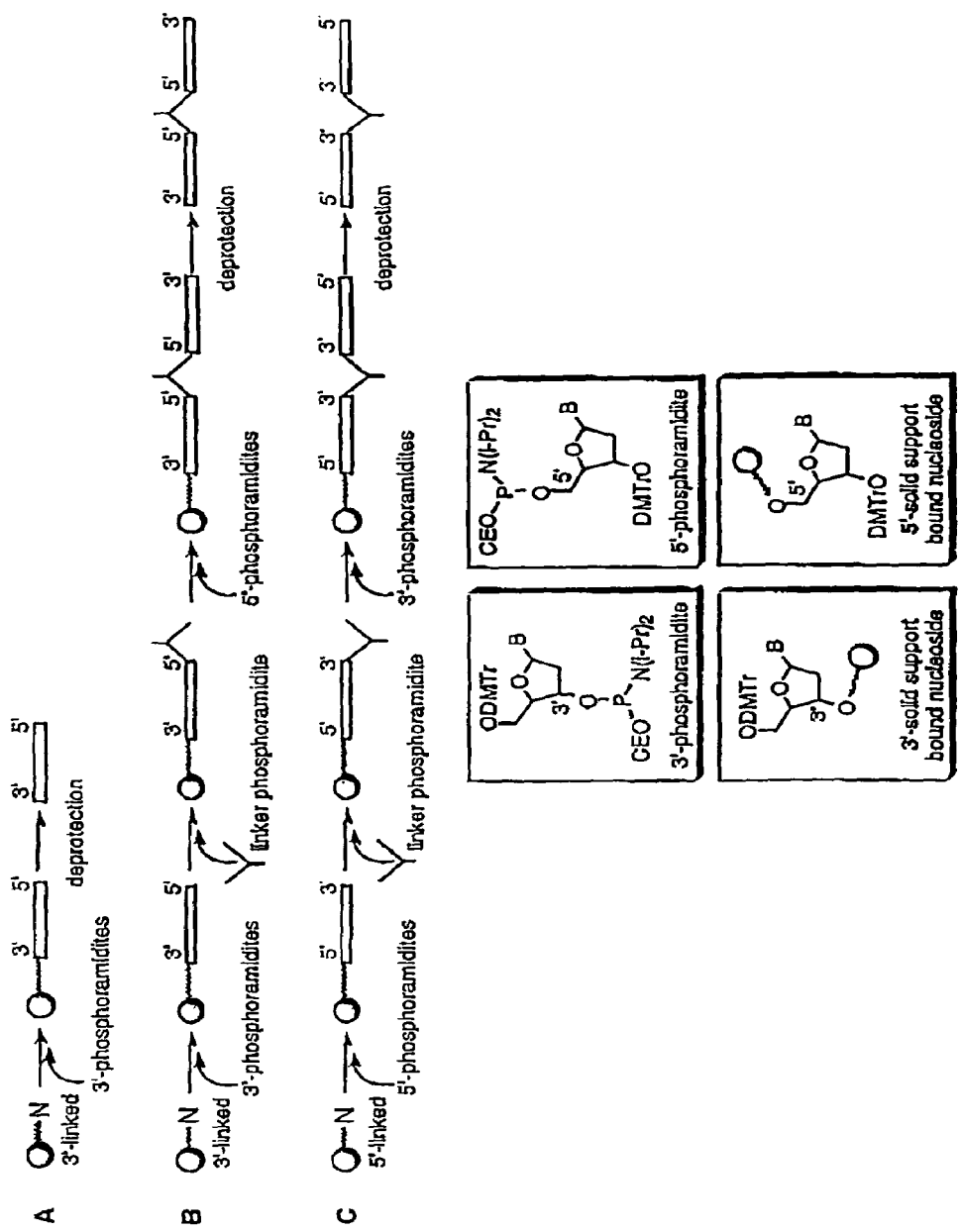
FIG. 5 is a synthetic scheme for the linear synthesis of immunomers of the invention. DMTr=4,4'-dimethoxytrityl; CE=cyanoethyl.
Figure 6:
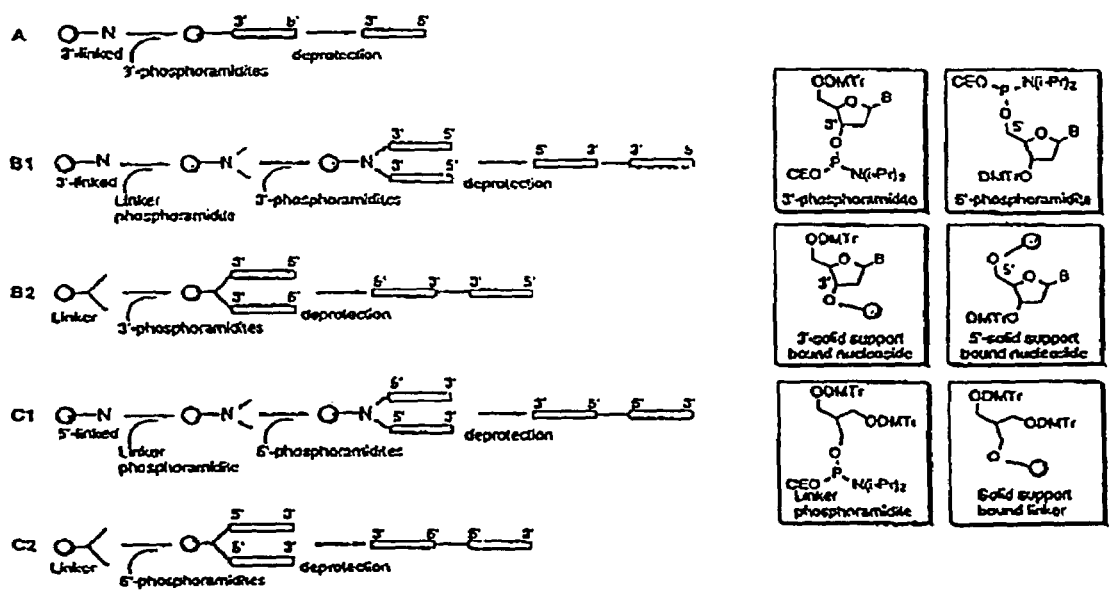
FIG. 6 is a synthetic scheme for the parallel synthesis of immunomers of the invention. DMTr=4,4'-dimethoxytrityl; CE=cyanoethyl.

The immunostimulatory oligonucleotides and/or immunomers used in the method according to the invention may conveniently be synthesized using an automated synthesizer and phosphoramidite approach as schematically depicted in FIGS. 5 and 6, and further described in the Examples. In some embodiments, the immunostimulatory oligonucleotides and/or immunomers are synthesized by a linear synthesis approach (see FIG. 5). As used herein, the term "linear synthesis" refers to a synthesis that starts at one end of the immunomer and progresses linearly to the other end. Linear synthesis permits incorporation of either identical or un-identical (in terms of length, base composition and/or chemical modifications incorporated) monomeric units into the immunostimulatory oligonucleotides and/or immunomers.

An alternative mode of synthesis for immunomers is "parallel synthesis", in which synthesis proceeds outward from a central linker moiety (see FIG. 6). A solid support attached linker can be used for parallel synthesis, as is described in U.S. Pat. No. 5,912,332. Alternatively, a universal solid support, such as phosphate attached to controlled pore glass support, can be used.

Parallel synthesis of immunomers has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunostimulatory oligonucleotides or immunomers used in the method according to the invention may conveniently be deprotected with concentrated ammonia solution or as recommended by the phosphoramidite supplier, if a modified nucleoside is incorporated. The product immunostimulatory oligonucleotides and/or immunomer is preferably purified by reversed phase HPLC, detritylated, desalted and dialyzed.

Table 4 shows representative immunomers used in the method according to the invention. Additional immunomers are found described in the Examples.

TABLE 4

Examples of Immunomer Sequences

| Oligo or Immunomer No. | Sequences and Modification (5'-3') |
|---|---|
| 1 (SEQ ID NO: 1) | 5'-GAGAACGCTCGACCTT-3' |
| 2 (SEQ ID NO: 1) | 5-GAGAACGCTCGACCTT-3'-3'-TTCCAGCTCGCAAGAG-5' |
| 3 (SEQ ID NO: 2) | 3'-TTCCAGCTCGCAAGAG-5'-5'-GAGAACGCTCGACCTT-3' |
| 4 (SEQ ID NO:2) | 5'-CTATCTGACGTTCTCTGT-3' |
| 5 (SEQ ID NO: 3) | 5'-T-3' branched to: HNCO—C₄H₈-5'-CTATLTGACGTTCCTCTGT-3' and HNCO—C₄H₈-5'-CTATLTGACGTTCCTCTGT-3' |
| 6 (SEQ ID NO: 3) | 5'-CTATLTGACGTTCTCTGT-3'-C₄H₈—CONH— and 5'-CTATLTGACGTTCTCTGT-3'-C₄H₈—CONH— joined 3'-C-5' |
| 7 (SEQ ID NO: 2) | 5'-CTATCTGACGTTCTCTGT-3'-C₄H₈—CONH— and 5'-CTATCTGACGTTCTCTGT-3'-C₄H₈—CONH— joined 3'-C-5' |
| 8 (SEQ ID NO: 2) | 5'-CTATCTGACGTTCTCTGT-3' and 5'-CTATCTGACGTTCTCTGT-3' joined 3'-C-5' |
| 9 (SEQ ID NO: 4) | 5'-CTATCTGAYCTTCTCTGT-3' and 5'-CTATCTGAYCTTCTCTGT-3' joined 3'-C-5' |
| 10 (SEQ ID NO: 5) | 5'-CTATCTGACRTTCTCTGT-3' and 5'-CTATCTGACRTTCTCTGT-3' joined 3'-C-5' |
| 11 (SEQ ID NO: 6) | 5'-CTALCTGAYGTTCTCTGT-3' and 5'-CTALCTGAYGTTCTCTGT-3' joined 3'-C-5' |

TABLE 4-continued

Examples of Immunomer Sequences

| Oligo or Immunomer No. | Sequences and Modification (5'-3') |
|---|---|
| 12 (SEQ ID NO: 7) | 5'-CTALCTGACRTTCTCTGT-3'⎤<br>⎣—3'-C-5'<br>5'-CTALCTGACRTTCTCTGT-3'⎦ |
| 13 (SEQ ID NO: 8 | 5-CTGACGTTCTCTGT-3' |
| 14 (SEQ ID NO: 8) | 5'-CTGACGTTCTCTGT-3'⎤<br>⎣—3'-C-5'<br>5'-CTGACGTTCTCTGT-3'⎦ |
| 15 (SEQ ID NO: 6) | 5'-CTGAYGTTCTCTGT-3'⎤<br>⎣—3'-C-5'<br>5'-CTGAYGTTCTCTGT-3'⎦ |
| 16 (SEQ ID NO: 7) | 5'-CTGACRTTCTCTGT-3'⎤<br>⎣—3'-C-5'<br>5'-CTGACRTTCTCTGT-3'⎦ |
| 17 (SEQ ID NO: 9 | 5'-XXTGACGTTCTCTGT-3' |
| 18 (SEQ ID NO: 10) | 5'-XXXTGACGTTCTCTGT-3'⎤<br>⎣—3'-C-5'<br>5'-XXXTGACGTTCTCTGT-3⎦ |
| 19 (SEQ ID NO: 11) | 5'-XXXTGAYGTTCTCTGT-3'⎤<br>⎣—3'-C-5'<br>5'-XXXTGAYGTTCTCTGT-3'⎦ |
| 20 (SEQ ID NO: 12) | 5'-XXXTGACRTTCTCTGT-3'⎤<br>⎣—3'-C-5'<br>5'-XXXTGACRTTCTCTGT-3'⎦ |
| 21 (SEQ ID NO: 13 | 5'-TCTGACGTTCT-3' |
| 22 (SEQ ID NO: 14) | 5'-XXXTCTGACGTTCT-3'⎤<br>⎣—3'-C-5'<br>5'-XXXTCTGACGTTCT-3'⎦ |
| 23 (SEQ ID NO: 15) | 5'-XXXTCTGAYGTTCT-3'⎤<br>⎣—3'-C-5'<br>5'-XXXTCTGAYGTTCT-3'⎦ |

TABLE 4-continued

Examples of Immunomer Sequences

| Oligo or Immunomer No. | Sequences and Modification (5'-3') |
|---|---|
| 24 (SEQ ID NO: 16) | 5'-XXXTCTGAYGTTCT-3'<br>———3'-C-5'<br>5'-XXXTCTGAYGTTCT-3' |

 = Symmetric longer branches; (NHCOC$_4$H$_8$)

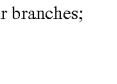 = Symmetric glycerol (short) branches

L = C3-alkyl linker;
X = 1',2'-dideoxyriboside;
Y = $^{5OH}$dC;
R = 7-deaza-dG

In a second aspect, the invention provides a method for treating cancer in a cancer patient comprising administering to the patient a chemotherapeutic agent in combination with an immunostimulatory oligonucleotide and/or immunomer conjugate, which comprises an immunostimulatory oligonucleotide and/or immunomer, as described above, and an antigen conjugated to the immunostimulatory oligonucleotide and/or immunomer at a position other than the accessible 5' end. In some embodiments, the non-nucleotidic linker comprises an antigen associated with cancer, which is conjugated to the oligonucleotide. In some other embodiments, the antigen is conjugated to the oligonucleotide at a position other than its 3' end. In some embodiments, the antigen produces a vaccine effect. For purposes of the invention, the term "associated with" means that the antigen is present when the cancer is present, but either is not present, or is present in reduced amounts, when the cancer is absent.

The immunostimulatory oligonucleotides and/or immunomer is covalently linked to the antigen, or it is otherwise operatively associated with the antigen. As used herein, the term "operatively associated with" refers to any association that maintains the activity of both immunostimulatory oligonucleotide and/or immunomer and antigen. Nonlimiting examples of such operative associations include being part of the same liposome or other such delivery vehicle or reagent. Additionally, a nucleic acid molecule encoding the antigen can be cloned into an expression vector and administered in combination with the immunostimulatory oligonucleotide and/or immunomer. As used herein, the term "vector" refers to a nucleic acid molecule capable of transporting another nucleic acid to which it has been linked. Preferred vectors are those capable of autonomous replication and expression of nucleic acids to which they are linked (e.g., an episome). Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In embodiments wherein the immunostimulatory oligonucleotide and/or immunomer is covalently linked to the antigen, such covalent linkage preferably is at any position on the immunostimulatory oligonucleotide and/or immunomer other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a third aspect, the invention provides pharmaceutical formulations comprising an immunostimulatory oligonucleotide and/or immunostimulatory oligonucleotide conjugate and/or immunomer or immunomer conjugate according to the invention, a chemotherapeutic agent and a physiologically acceptable carrier. As used herein, the term "physiologically acceptable" refers to a material that does not interfere with the effectiveness of the immunomer and is compatible with a biological system such as a cell, cell culture, tissue, or organism. Preferably, the biological system is a living organism, such as a vertebrate. Preferred chemotherapeutic agents include, without limitation Gemcitabine methotrexate, vincristine, adriamycin, cisplatin, non-sugar containing chloroethylnitrosoureas, 5-fluorouracil, mitomycin C, bleomycin, doxorubicin, dacarbazine, Taxol®, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/ Lometexol, Glamolec, CI994, TNP-470, Hycamtin/Topotecan, PKC412, Valspodar/PSC833, Novantrone®/Mitroxantrone, Metaret/Suramin, Batimastat, E7070, BCH-4556, CS-682, 9-AC, AG3340, AG3433, InceUVX-710, VX-853, ZD0101, IS1641, ODN 698, TA 2516/Marmistat, BB2516/ Marmistat, CDP 845, D2163, PD183805, DX8951f, Lemonal DP 2202, FK 317, imatinib mesylate/Gleevec®, Picibanil/OK-432, AD 32/Valrubicin, Metastron®/strontium derivative, Temodal/Temozolomide, EvacetAiposomal doxorubicin, Yewtaxan/Placlitaxel, Taxol®/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol®/Levamisole, Eniluracil/776C85/5FU enhancer, Campto/Levamisole, Camptosar®/Irinotecan, Tumodex/Ralitrexed, Leustatin®/Cladribine, Paxex/Paclitaxel, Doxil®/liposomal doxorubicin, Caelyx/liposomal doxorubicin, Fludara®/Fludarabine, Pharmarubicin/Epirubicin, DepoCyt®, ZD 1839, LU 79553/Bis-Naphtalimide, LU 103793/Dolastain, Caetyx/liposomal doxorubicin, Gemzar®/Gemcitabine, ZD 0473/Anormed®, YM 116, Iodine seeds, CDK4 and CDK2 inhibitors, PARP inhibitors, D4809/Dexifosamide, Ifes/Mesnex®/Ifosamide, Vumon®/Teniposide, Paraplatin®/Carboplatin, Plantinol/cisplatin, Vepeside/Etoposide, ZD 9331, Taxotere®/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In yet another embodiment, the formulations include a cancer vaccine selected from the group consisting of EFG, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-vased vaccine, PACIS, BCG vaccine, TA-HPV, TA-CIN, DISC-virus and ImmunCyst/TheraCys.

In a further aspect, the invention provides a method for treating cancer in a cancer patient comprising administering to the patient a monoclonal antibody in combination with an immunostimulatory oligonucleotide and/or immunomer, as described herein. Passive immunotherapy in the form of antibodies, and particularly monoclonal antibodies, has been the subject of considerable research and development as anti-cancer agents. The term "monoclonal antibody" as used herein refers to an antibody molecule of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. Examples of anti-cancer agents include, but are not limited to, Panorex® (Glaxo-Welicome), Rituxan® (IDEC/Genentech/Hoffman la Roche), Mylotarg® (Wyeth), Campath® (Millennium), Zevalin® (IDEC and Schering AG), Bexxar® (Corixa/GSK), Erbitux® (Imclone/BMS), Avastin® (Genentech) and Herceptin ® (Genentech/Hoffman la Roche). Antibodies may also be employed in active immunotherapy utilising anti-idiotype antibodies which appear to mimic (in an immunological sense) cancer antigens. Monoclonal antibodies can be generated by methods known to those skilled in the art of recombinant DNA technology.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences*, 18th Edition, ed. A. Gennaro, Mack Publishing Co., Easton, Pa., 1990.

The invention provides a kit comprising a chemotherapeutic agent, and immunostimulatory oligonucleotides and/or immunomers, the latter comprising at least two oligonucleotides linked together, such that the immunomer has more than one accessible 5' end, wherein at least one of the oligonucleotides is an immunostimulatory oligonucleotide. In another aspect, the kit comprises an immunostimulatory oligonucleotide and/or immunostimulatory oligonucleotide conjugate and/or immunomer or immunomer conjugate according to the invention, a chemotherapeutic agent and a physiologically acceptable carrier. The kit will generally also include a set of instructions for use.

The combination of immunomer structure with synthetic stimulatory motifs, for example CpR (R=2'-deoxy-7-deazaguanosine), induced different cytokine expression profiles than without synthetic stimulatory motifs. As a result, IMO compounds not only cause less adverse reactions frequently seen with whole bacterial products but also elicit more specific immune responses depending on the type of cancer.

Repeated peritumoral application of IMO compounds resulted in strong inhibition or eradication of established syngeneic tumors CT26.CL25 and B16.F0. Peritoneal administration of IMO motifs also suppressed disseminated B 16.F0, CT26.WT or CT26.CL25 tumor growth in the peritoneal cavity. Several immunological properties of IMO compounds account for this therapeutic effect. Without wishing to be bound to any particular theory, IMO motifs possibly induce rapid, acute phase reactions around tumor nodules, including recruitment and activation of macrophages, dendritic and NK cells and induction of cytokine secretion. Consistent with activation of immune cells, serum IL-12 and circulating NK and macrophage cells markedly increased within 4 hr and persisted for 24 hr following IMO administration (data not shown). Such elevated cellular immune responses could create a hostile environment for tumor cells. Further, the destruction of tumor cells in such environment provides tumor antigens to nearby dendritic cells (DCs) and macrophages. IMO compounds are shown to directly and rapidly promote antigen presentation by DCs and functional maturation of macrophages increasing surface expression of MHC and costimulatory molecules. The activated antigen presenting cells then lead to a strong adaptive T lymphocyte-mediated specific immune response in tumor bearing mice.

Besides the innate immunity, the treatment of mice bearing CT26 colon tumor resulted in the development of strong adaptive immune responses. First, the IMO treatment of mice bearing tumors expressing β-gal as a model antigen showed strong MHC class I restricted specific T cell responses. Second, tumor bearing mice treated with IMO compounds were specifically protected against subsequent challenge with the same tumor cells, suggesting the involvement of memory T lymphocytes. Thirdly, naïve mice adoptively transferred with splenic cells obtained from tumor bearing mice treated with IMO compounds developed specific antitumor immunity and rejected the same tumor challenge.

Th2-type cytokines down-regulate antitumor immunity, and the activation of Th 1 cell responses can enhance antitumor immunity. Therefore, a shift to Th 1-type cytokine production could be a plausible approach for immunotherapy of cancers as well as treating viral infections. High levels of Th-2 cytokine, IL4, are found in cultures of spleen cells obtained from either PBS or non-CpG DNA control treated CT26.CL25 tumor bearing mice. In contrast, splenocytes from IMO treated mice bearing the same tumor produced higher IFN-γ, indicating IMO compounds can reverse Th2-type cytokine production to Th 1 responses in tumor bearing mice. Furthermore, IMO therapy induced a 5-fold increase (OD units) in the levels of circulating β-gal specific IgG2a, resulting in a significant increase in IgG2a/IgG1 ratio. Additionally, IL-12 ko mice failed to respond to IMO treatment suggesting a role for this Th-1 cytokine in IMO antitumor activity. Taken together, this clearly indicates that IMO compounds strongly activate Th1 immune responses in tumor bearing mice.

Major limitations for chemotherapy alone or as a follow-up treatment after surgery are toxicity and drug resistance. Immunotherapy when combined with surgery and chemotherapy may have advantages to clear the residual tumor cells and reduce the drug dose. This is especially true for IMO-based immunotherapy as it activated both innate and adaptive immune systems. IMO treatment may overcome the immune suppressive effects of chemotherapeutic agents as evidenced by significant increase in CD69+ and CD86+cells in IMO 2-docetaxel combination treated tumor bearing mice compared with tumor bearing mice treated with docetaxel only. Effects of conventional chemotherapy using docetaxel or doxorubicin in B16.F0 melanoma or 4T1 breast carcinoma bearing mice respectively were markedly enhanced when combined with IMO compounds.

Taken together, the current results suggest that IMO compounds induced strong immunopharmacological and antitumor effects in vivo. Tumor experiments in knockout mice suggest that Th1 cytokine, IL-12, is required for IMO induced antitumor effects. Moreover, the treatment with IMO compounds not only resulted in tumor regression, but also led to the development of strong tumor specific adaptive immune responses. Additionally, human specific IMO compounds show potent antitumor activity in syngeneic tumor models. A synergistic effect was found with the combination of chemotherapy agents and IMO treatment. Moreover, IMO compounds showed immune cell activation following chemotherapy, suggesting combination therapy as a means for overcoming immune suppression induced by chemotherapy. No IMO treatment-related toxicity was observed in mice in any tumor model at the doses studied.

The examples below are intended to further illustrate certain preferred embodiments of the invention, and are not intended to limit the scope of the invention.

EXAMPLES

Example 1

Synthesis of Oligonucleotides Containing Immunomodulatory Moieties

Oligonucleotides were synthesized on a 1 μmol scale using an automated DNA synthesizer (Expedite 8909; PerSeptive Biosystems, Framingham, Mass.), following the linear synthesis or parallel synthesis procedures outlined in FIGS. 5 and 6.

Deoxyribonucleoside phosphoramidites were obtained from Applied Biosystems (Foster City, Calif.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). β-L-2'-deoxyribonucleoside phosphoramidite, α-2'-deoxyribonucleoside phosphoramidite, mono-DMT-glycerol phosphoramidite and di-DMT-glycerol phosphoramidite were obtained from ChemGenes (Ashland, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Hybridon, Inc. (Cambridge, Mass.) (Noronha et al. (2000) *Biochem.*, 39:7050-7062).

All nucleoside phosphoramidites were characterized by $^{31}$p and $^1$H NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Analysis of Spleen Cell Proliferation

Figure 8A:
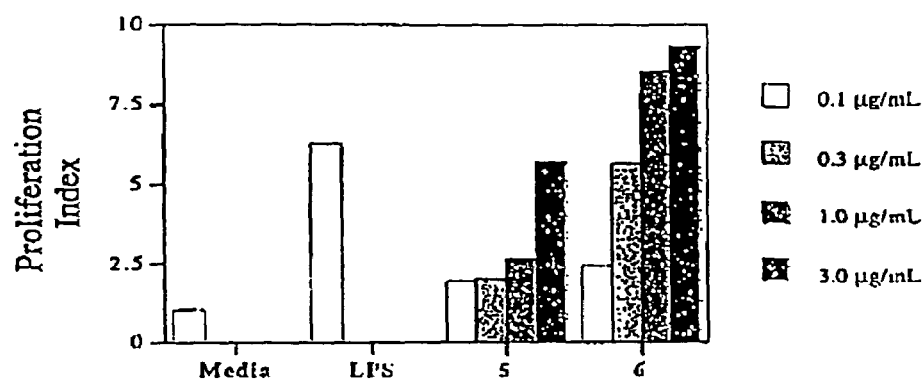
FIG. 8A is a graphic representation of the induction of BALB/c mouse spleen cell proliferation in cell cultures by different concentrations of Immunomers 5 and 6, which have inaccessible and accessible 5'-ends, respectively.

In vitro analysis of splenocyte proliferation was carried out using standard procedures as described previously (see, e.g., Zhao et al., Biochem Pharma 51:173-182 (1996)). The results are shown in FIG. 8A. These results demonstrate that at the higher concentrations, Immunomer 6, having two accessible 5' ends results in greater splenocyte proliferation than does Immunomer 5, having no accessible 5' end or Oligonucleotide 4, with a single accessible 5' end. Immunomer 6 also causes greater splenocyte proliferation than the LPS positive control.

Example 3

In vivo Splenomegaly Assays

Figure 8B:
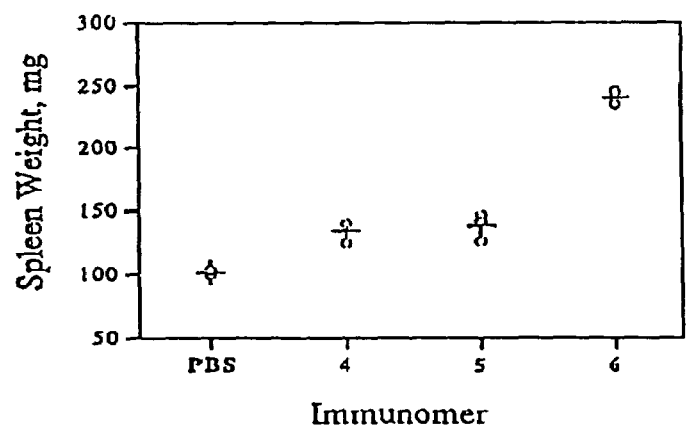
FIG. 8B is a graphic representation of BALB/c mouse spleen enlargement by Oligonucleotide 4 and Immunomers 5-6, which have an immunogenic chemical modification in the 5'-flanking sequence of the CpG motif. Again, the immunomer, which has accessible 5'-ends (6), has a greater ability to increase spleen enlargement compared with Immunomer 5, which does not have accessible 5'-end and with monomeric Oligonucleotide 4.
Figure 9A:
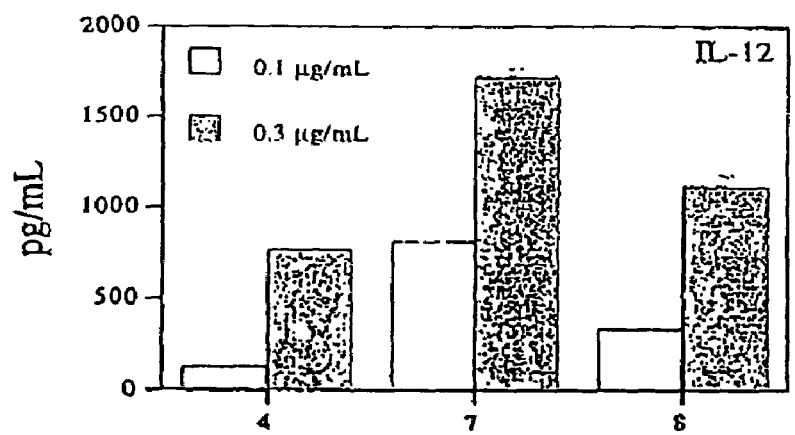
FIG. 9A is a graphic representation of induction of IL-12 by different concentrations of Oligonucleotide 4 and Immunomers 7 and 8 in BALB/c mouse spleen cell cultures.
Figure 9B:
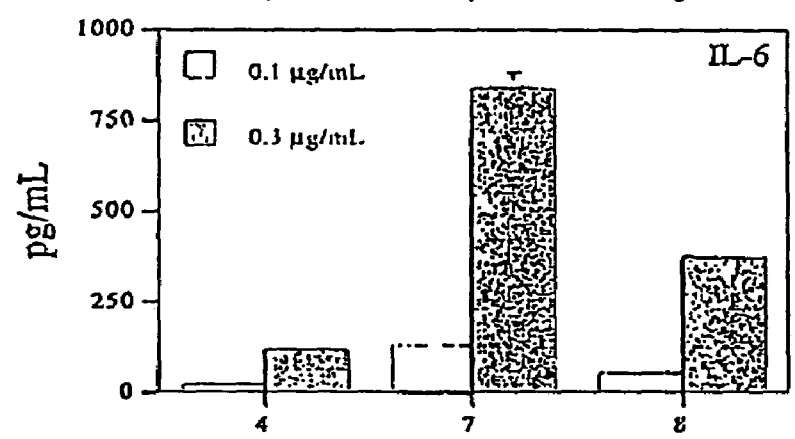
FIG. 9B is a graphic representation of induction of IL-6 by different concentrations of Oligonucleotide 4 and Immunomers 7 and 8 in BALB/c mouse spleen cell cultures.
Figure 9C:
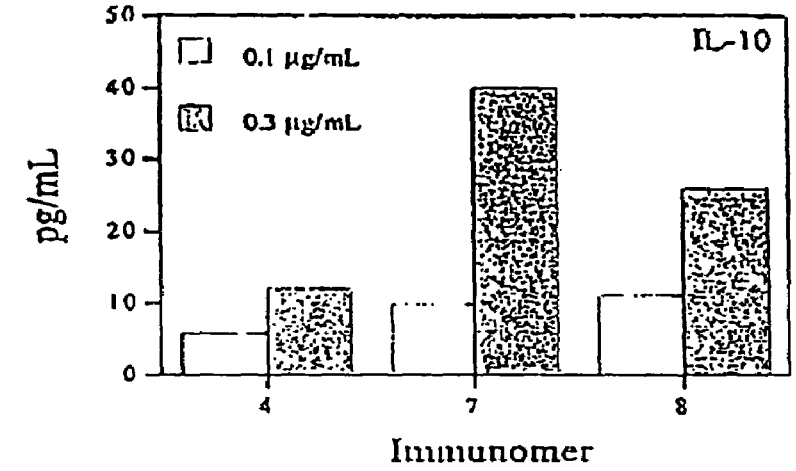
FIG. 9C is a graphic representation of induction of IL-10 by different concentrations of Oligonucleotide 4 and Immunomers 7 and 8 in BALB/c mouse spleen cell cultures.
Figure 10A:
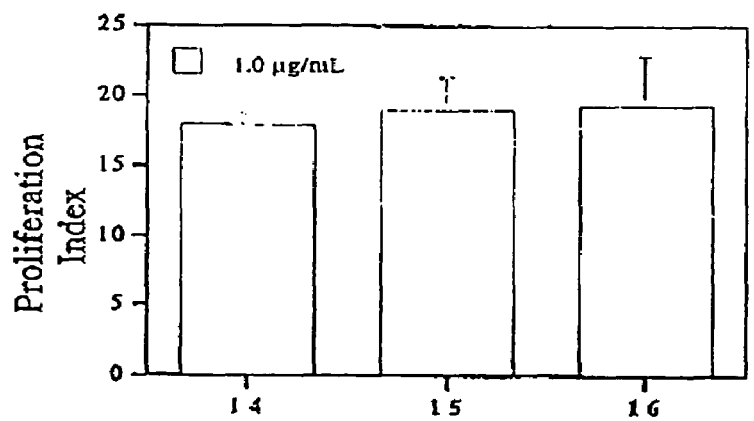
FIG. 10A is a graphic representation of the induction of cell proliferation by Immunomers 14, 15, and 16 in BALB/c mouse spleen cell cultures.
Figure 10B:
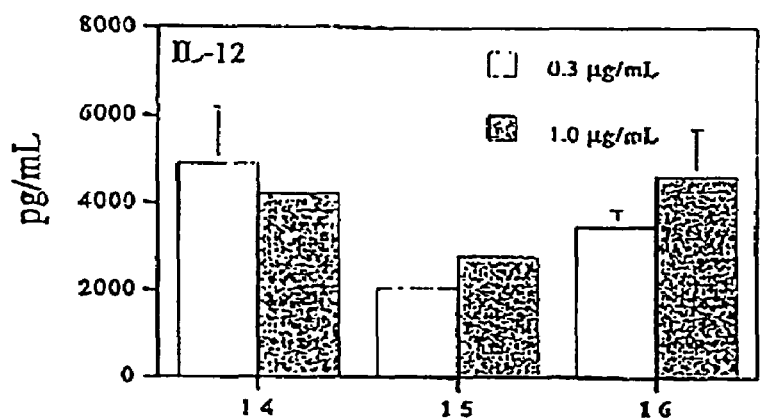
FIG. 10B is a graphic representation of the induction of cell proliferation by IL-12 by different concentrations of Immunomers 14 and 16 in BALB/c mouse spleen cell cultures.
Figure 10C:
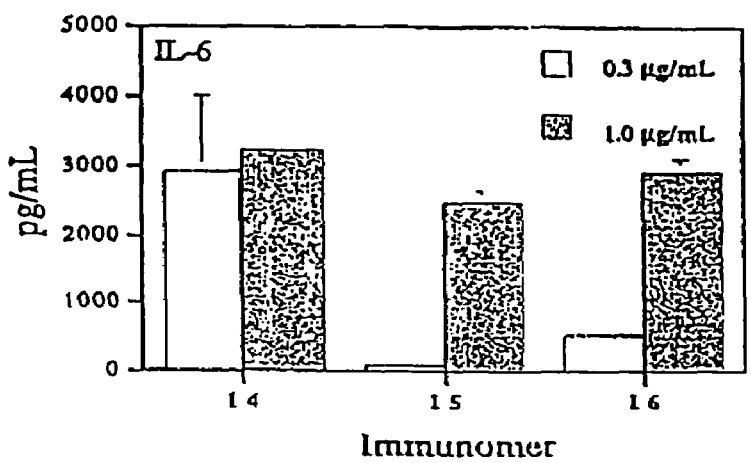
FIG. 10C is a graphic representation of the induction of cell proliferation by IL-6 by different concentrations of Immunomers 14 and 16 in BALB/c mouse spleen cell cultures.
Figure 11A:
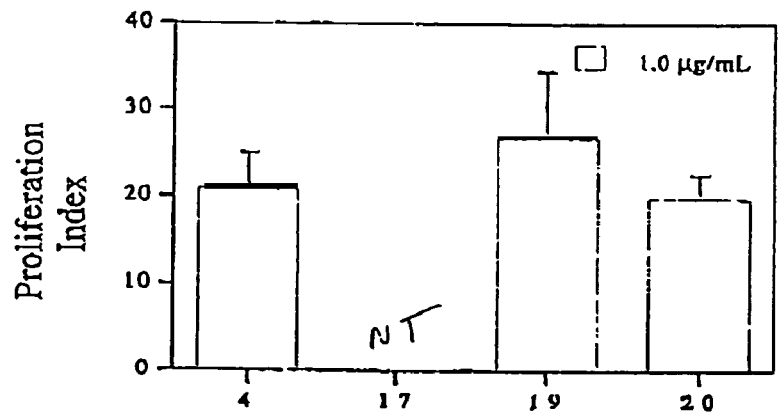
FIG. 11A is a graphic representation of the induction of cell proliferation by Oligonucleotides 4 and 17 and Immunomers 19 and 20 in BALB/c mouse spleen cell cultures.
Figure 11B:
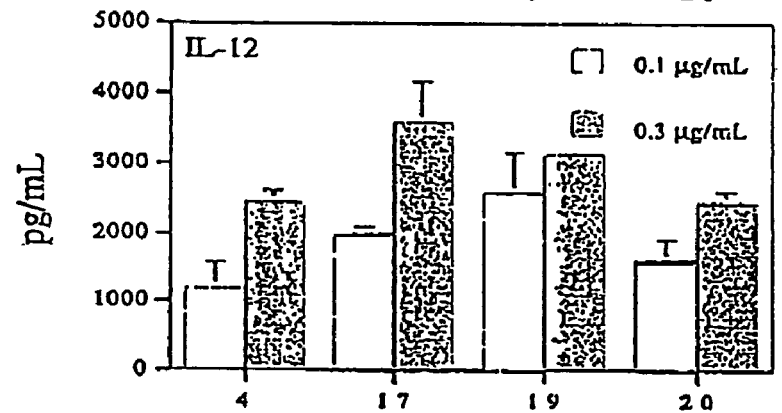
FIG. 11B is a graphic representation of the induction of cell proliferation IL-12 by different concentrations of Oligonucleotides 4 and 17 and Immunomers 19 and 20 in BALB/c mouse spleen cell cultures.
Figure 11C:
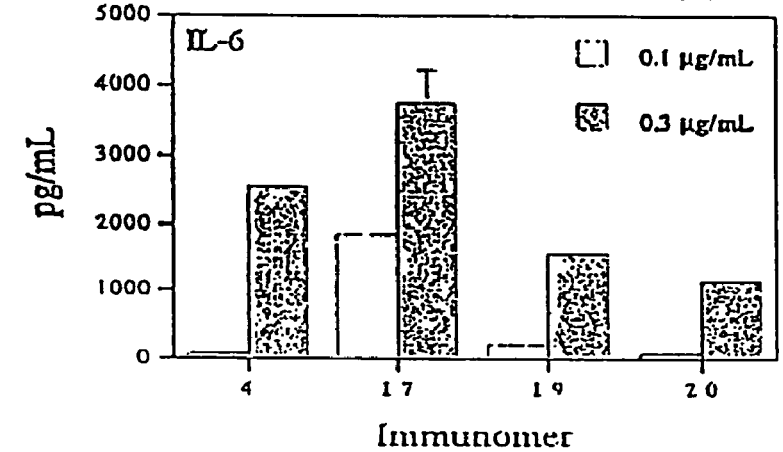
FIG. 11C is a graphic representation of the induction of cell proliferation IL-6 by different concentrations of Oligonucleotides 4 and 17 and Immunomers 19 and 20 in BALB/c mouse spleen cell cultures.
Figure 12:
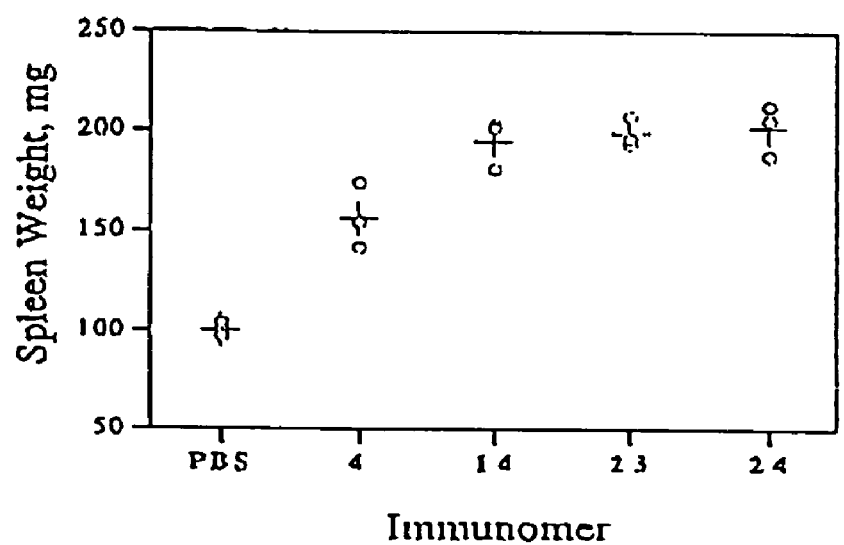
FIG. 12 is a graphic representation of BALB/c mouse spleen enlargement using Oligonucleotide 4 and Immunomers 14, 23, and 24.

To test the applicability of the in vitro results to an in vivo model, selected oligonucleotides were administered to mice and the degree of splenomegaly was measured as an indicator of the level of immunostimulatory activity. A single dose of 5 mg/kg was administered to BALB/c mice (female, 4-6 weeks old, Harlan Sprague Dawley Inc, Baltic, Conn.) intraperitoneally. The mice were sacrificed 72 hours after oligonucleotide administration, and spleens were harvested and weighed. The results are shown in FIG. 8B. These results demonstrate that Immunomer 6, having two accessible 5' ends, has a far greater immunostimulatory effect than do Oligonucleotide 4 or Immunomer 5.

Example 4

Cytokine Analysis

The secretion of IL-12 and IL-6 in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 μg/mL in PBSN buffer (PBS/0.05% sodium azide, pH 9.6) overnight at 4° C. and then blocked with PBS/i % BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 μg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments). The results are shown in Table 5A below.

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Hemdon, Va.) and supplemented with 10% heat inactivated FCS and penicillin-streptomycin (100 U/ml). Cells were cultured in 24 well plates for different time periods at $1\times10^6$ cells/ml/well in the presence or absence of oligonucleotides. At the end of the incubation period, supernatants were harvested and stored frozen at −70° C. until assayed for various cytokines including IL-6 (BD Pharmingen, San Diego, Calif.), IL-10 (BD Pharmingen), IL-12 (BioSource International, Camarillo, Calif.), IFN-α (BioSource International) and -γ(BD Pharmingen) and TNF-α(BD Pharmingen) by sandwich ELISA. The results are shown in Table 5 below.

In all instances, the levels of IL-12 and IL-6 in the cell culture supernatants were calculated from the standard curve constructed under the same experimental conditions for IL-112 and IL-6, respectively. The levels of IL-10, IFN-gamma and TNF-α in the cell culture supernatants were calculated from the standard curve constructed under the same experimental conditions for IL-10, IFN-gamma and TNF-α, respectively.

TABLE 5

Immunomer Structure and Immunostimulatory Activity in Human PBMC Cultures

| Oligo No. | Sequences and Modification (5'-3') | Oligo Length/ or Each Chain | IL-12 (pg/mL) D1 | IL-12 (pg/mL) D2 | IL-6 (pg/mL) D1 | IL-6 (pg/mL) D2 |
|---|---|---|---|---|---|---|
| 25 (SEQ ID NO: 17) | 5'-CTATCTGTCGTTCTCTGT-3' | 18mer (PS) | 184 | 332 | 3077 | 5369 |
| 26 (SEQ ID NO: 18) | 5'-TCTGTCR$_1$TTCT-3'  \\X$_1$  5'-TCTGTCR$_1$TTCT-3' | 11mer (PS) | 237 | 352 | 3724 | 4892 |

| Oligo No. | Sequences and Modification (5'-3') | Oligo Length/ or Each Chain | IL-10 (pg/mL) D1 | IL-10 (pg/mL) D2 | IFN-γ (pg/mL) D1 | IFN-γ (pg/mL) D2 |
|---|---|---|---|---|---|---|
| 25 (SEQ ID NO: 17) | 5'-CTATCTGTCGTTCTCTGT-3' | 18mer (PS) | 37 | 88 | 125 | 84 |
| 26 (SEQ ID NO: 18) | 5'-TCTGTCR$_1$TTCT-3'  \\X$_1$  5'-TCTGTCR$_1$TTCT-3' | 11mer (PS) | 48 | 139 | 251 | 40 |

| Oligo No. | Sequences and Modification (5'-3') | Oligo Length/ or Each Chain | TNF-α(pg/mL) D1 | TNF-α(pg/mL) D2 |
|---|---|---|---|---|
| 25 (SEQ ID NO: 17) | 5'-CTATCTGTCGTTCTCTGT-3' | 18mer (PS) | 537 | nt |
| 26 (SEQ ID NO: 18) | 5'-TCTGTCR$_1$TTCT-3'  \\X$_1$  5'-TCTGTCR$_1$TTCT-3' | 11mer (PS) | 681 | nt |

D1 and D2 are donors 1 and 2.

TABLE 5A

Immunomer Structure and Immunostimulatory Activity in BALB/c Mouse Spleen Cell Cultures

| Oligo No. | Sequences and Modification (5'-3') | Oligo Length/ Or Each Chain | IL-12 (pg/mL) 3 µg/mL | IL-6 (pg/mL) 10 µg/mL |
|---|---|---|---|---|
| 26 (SEQ ID NO: 18) | 5'-TCTGTCR$_1$TTCT-3'<br>          \\$X_1$<br>5'-TCTGTCR$_1$TTCT-3' | 11mer (PS) | 870 | 10670 |
| 27 (SEQ ID NO: 19) | 5'-TCTGTCR$_2$TTCT-3'<br>          \\$X_1$<br>5'-TCTGTCR$_2$TTCT-3' | 11mer (PS) | 1441 | 7664 |
| 28 (SEQ ID NO: 20) | 5'-TCTGTY$_2$R$_2$TTCT-3'<br>          \\$X_1$<br>5'-TCTGTY$_2$R$_2$TTCT-3' | 11mer (PS) | 1208 | 1021 |
| 29 (SEQ ID NO: 21) | 5'-XXTCTGTCR$_1$TTCT-3'<br>          \\$X_1$<br>5'-XXTCTGTCR$_1$TTCT-3' | 11mer (PS) | 162 | 1013 |
| 30 (SEQ ID NO: 22) | 5'-CTGTCR$_2$TTCTCTGT-3'<br>          \\$X_1$<br>5'-CTGTCR$_2$TTCTCTGT-3' | 14mer (PO) | 264 | 251 |
| 31 (SEQ ID NO: 23) | 5'-CTGTY$_2$R$_2$TTCTCTGT-3'<br>          \\$X_1$<br>5'-CTGTY$_2$R$_2$TTCTCTGT-3' | 14mer (PO) | 149 | 119 |
| 32 (SEQ ID NO: 24) | 5'-TCTGACR$_1$TTCT-3'<br>          \\$X_1$<br>5'-TCTGACR$_1$TTCT-3' | 11mer (PS) | 2520 | 9699 |
| 33 (SEQ ID NO: 25) | 5'-XXTCTGACR$_1$TTCT-3'<br>          \\$X_1$<br>5'-XXTCTGACR$_1$TTCT-3' | 11mer (PS) | 2214 | 16881 |
| 34 (SEQ ID NO: 26) | 5'-TCTGACR$_2$TTCT-3'<br>          \\$X_1$<br>5'-TCTGACR$_2$TTCT-3' | 11mer PS) | 3945 | 10766 |
| 35 (SEQ ID NO: 27) | 5'-TCTGAY$_2$R$_2$TTCT-3'<br>          \\$X_1$<br>5'-TCTGAY$_2$R$_2$TTCT-3' | 11mer (PS) | 2573 | 19411 |
| 36 (SEQ ID NO: 28) | 5'-CTGAY$_2$GTTCTCTGT-3'<br>          \\$X_1$<br>5'-CTGAY$_2$GTTCTCTGT-3' | 14mer (PO) | 2699 | 408 |
| 37 (SEQ ID NO: 29) | 5'-CTGACR$_2$TTCTCTGT-3'<br>          \\$X_1$<br>5'-CTGACR$_2$TTCTCTGT-3' | 14mer (PO) | 839 | 85 |

TABLE 5A-continued

Immunomer Structure and Immunostimulatory Activity in BALB/c Mouse Spleen Cell Cultures

| Oligo No. | Sequences and Modification (5'-3') | Oligo Length/ Or Each Chain | IL-12 (pg/mL) 3 μg/mL | IL-6 (pg/mL) 10 μg/mL |
|---|---|---|---|---|
| 38 (SEQ ID NO: 30) | 5'-CTGAY$_2$R$_2$TTCTCTGT-3'⟩X$_1$ 5'-CTGAY$_2$R$_2$TTCTCTGT-3'⟩ | 14mer (PO) | 143 | 160 |

Normal phase represents a phosphorothioate linkage; Italic phase represents a phosphodiester linkage.

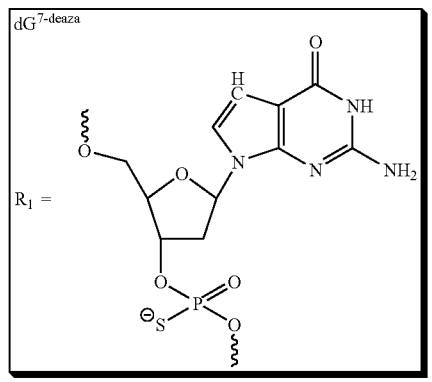

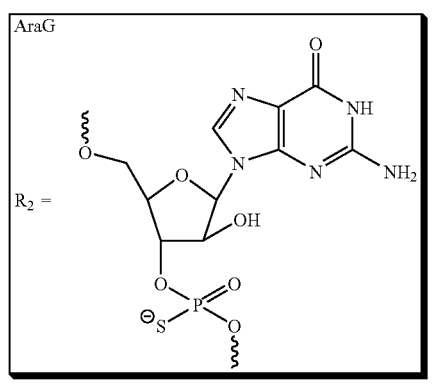

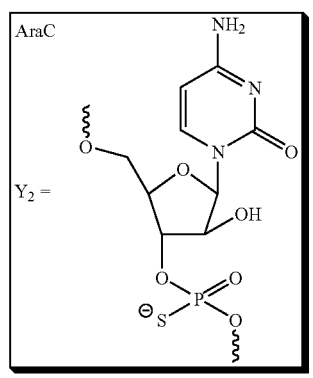

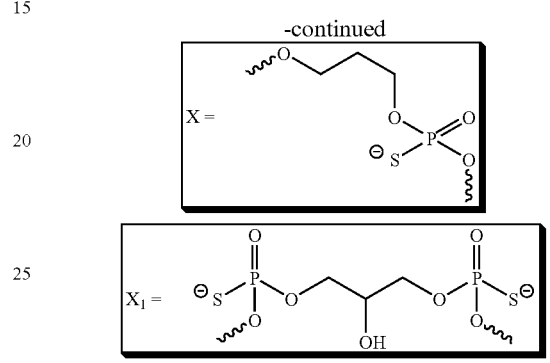

Figure 7A:
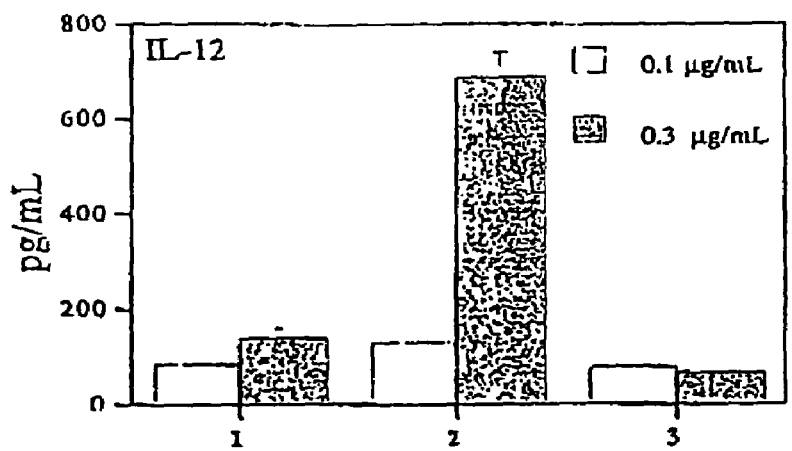
FIG. 7A is a graphic representation of the induction of IL-12 by Oligonucleotide 1 and Immunomers 2-3 in BALB/c mouse spleen cell cultures. These data suggest that Immunomer 2, which has accessible 5'-ends, is a stronger inducer of IL-12 than monomeric Oligo 1, and that Immunomer 3, which does not have accessible 5'-ends, has equal or weaker ability to produce immune stimulation compared with oligo 1.
Figure 7B:
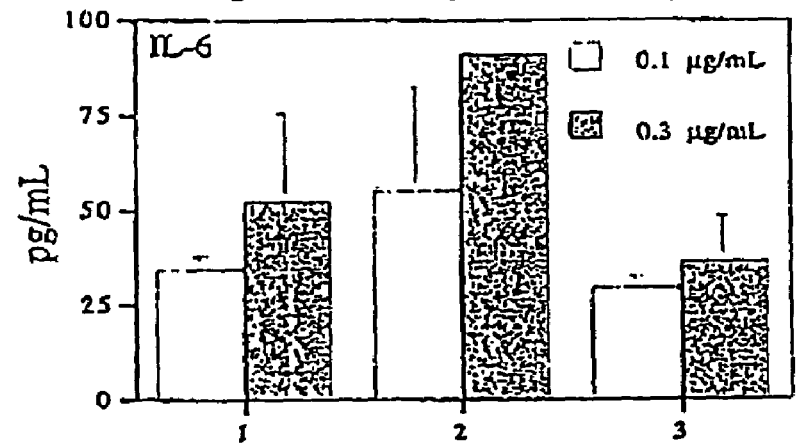
FIG. 7B is a graphic representation of the induction of IL-6 (top to bottom, respectively) by Oligonucleotide 1 and Immunomers 2-3 in BALB/c mouse spleen cells cultures. These data suggest that Immunomer 2, which has accessible 5'-ends, is a stronger inducer of IL-6 than monomeric Oligo 1, and that Immunomer 3, which does not have accessible 5'-ends, has equal or weaker ability to induce immune stimulation compared with Oligo 1.
Figure 7C:
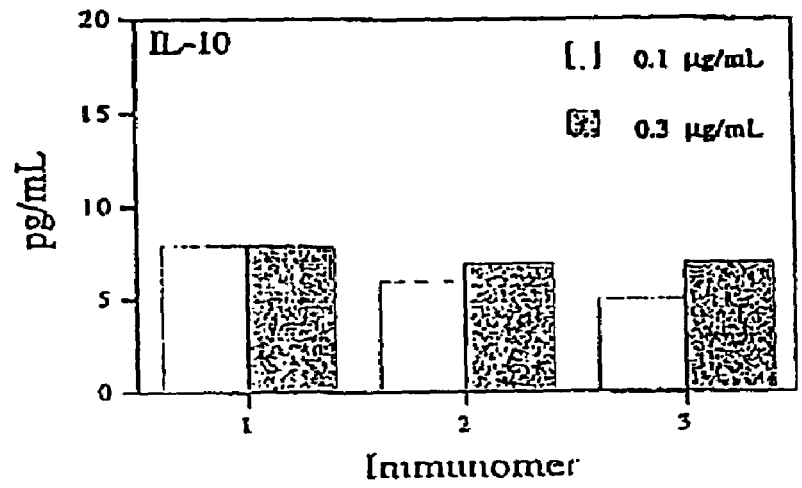
FIG. 7C is a graphic representation of the induction of IL-10 by Oligonucleotide 1 and Immunomers 2-3 (top to bottom, respectively) in BALB/c mouse spleen cell cultures.

In addition, the results shown in FIGS. 7A-C demonstrate that Immunomer 2, with two accessible 5' ends elevates IL-12 and IL-6, but not IL-10 at lower concentrations than Oligo-nucleotides 1 or 3, with one or zero accessible 5' ends, respectively.

Example 5

Immunostimulatory Activity of Immunomers Containing A Non-Natural Pyrimidine or Non-Natural Purine Nucleoside As shown in Tables 9-11, immunostimulatory activity was maintained for immunomers of various lengths having a non-natural pyrimidine nucleoside or non-natural purine nucleoside in the immunostimulatory dinucleotide motif.

TABLE 9

Immunomer Structure and Immunostimulatory Activity

| No. | Sequences and Modification (5'-3') | Oligo Length/ or Each Chain | IL-12 (pg/mL) @ 3 μg/mL | IL-6 (pg/mL) @ 3 μg/mL |
|---|---|---|---|---|
| 51 (SEQ ID NO: 31) | 5'-CTCACTTTCGTTCTCTGT-3' | 18mer | 404 | 348 |
| 57 (SEQ ID NO: 32) | 5'-TCTTTYGTTCT-3'⟩3'-T-5' 5'-TCTTTYGTTCT-3'⟩ | 11mer | 591 | 365 |

TABLE 9-continued

Immunomer Structure and Immunostimulatory Activity

| No. | Sequences and Modification (5'-3') | Oligo Length/ or Each Chain | IL-12 (pg/mL) @ 3 µg/mL | IL-6 (pg/mL) @ 3 µg/mL |
|---|---|---|---|---|
| 58 (SEQ ID NO: 33) | 5'-TCTTTCRTTCT-3'⎯⎤<br>                            ⎦3'-T-5'<br>5'-TCTTTCRTTCT-3'⎯⎦ | 11mer | 303 | 283 |
| 59 N/A | 5'-TTYGTTCT-3'⎯⎤<br>                       ⎦3'-T-5'<br>5'-TTYGTTCT-3'⎯⎦ | 8mer | 55 | 66 |
| 60 N/A | 5'-TTCRTTCT-3'⎯⎤<br>                       ⎦3'-T-5'<br>5'-TTCRTTCT-3'⎯⎦ | 8mer | 242 | 143 |

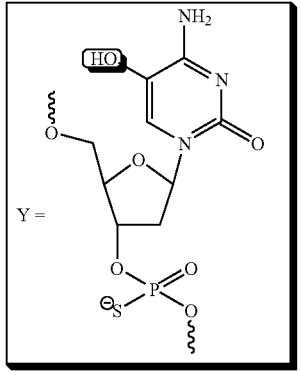

TABLE 10

Immunomer Structure and Immunostimulatory Activity

| No. | Sequences and Modification (5'-3') | Oligo Length/ or Each Chain | IL-12 (pg/mL) 3 µg/mL | IL-6 (pg/mL) 3 µg/mL |
|---|---|---|---|---|
| 25 (SEQ ID NO: 17) | 5'-CTATCTGTCGTTCTCTGT-3' | 18mer | 379 | 339 |

TABLE 10-continued

Immunomer Structure and Immunostimulatory Activity

| No. | Sequences and Modification (5'-3') | Oligo Length/ or Each Chain | IL-12 (pg/mL) 3 µg/mL | IL-6 (pg/mL) 3 µg/mL |
|---|---|---|---|---|
| 61 (SEQ ID NO: 34) | 5'-TCTGTYGTTCT-3'⎯⎤<br>                              ⎦3'-T-5'<br>5'-TCTGTYGTTCT-3'⎯⎦ | 11mer | 1127 | 470 |
| 62 (SEQ ID NO: 35) | 5'-TCTGTCRTTCT-3'⎯⎤<br>                              ⎦3'-T-5'<br>5'-TCTGTCRTTCT-3'⎯⎦ | 11mer | 787 | 296 |
| 63 N/A | 5'-GTYGTTCT-3'⎯⎤<br>                       ⎦3'-T-5'<br>5'-GTYGTTCT-3'⎯⎦ | 8mer | 64 | 126 |
| 64 N/A | 5'-GTCRTTCT-3'⎯⎤<br>                       ⎦3'-T-5'<br>5'-GTCRTTCT-3'⎯⎦ | 8mer | 246 | 113 |

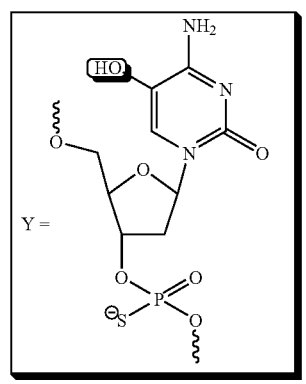

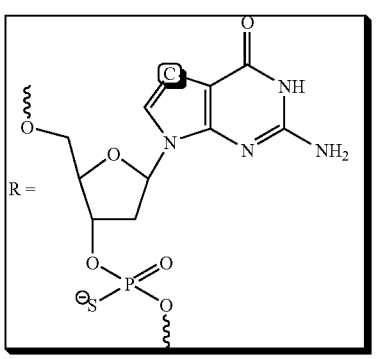

TABLE 11

Immunomer Structure and Immunostimulatory Activity

| No. | Sequences and Modification (5'-3') | Oligo Length/or Each Chain | IL-12 (pg/mL) 3 µg/mL | IL-6 (pg/mL) 3 µg/mL |
|---|---|---|---|---|
| 4 (SEQ ID NO: 2) | 5'-CTATCTGACGTTCTCTGT-3' | 18mer | 1176 | 1892 |
| 65 (SEQ ID NO: 4) | 5'-CTATCTGAYGTTCTCTGT-3'<br>5'-CTATCTGAYGTTCTCTGT-3'  ⎤-3'-T-5' | 18mer | 443 | 192 |
| 66 (SEQ ID NO: 5) | 5'-CTATCTGACRTTCTCTGT-3'<br>5'-CTATCTGACRTTCTCTGT-3'  ⎤-3'-T-5' | 18mer | 627 | 464 |
| 67 (SEQ ID NO: 6) | 5'-CTGAYGTTCTCTGT-3'<br>5'-CTGAYGTTCTCTGT-3'  ⎤-3'-T-5' | 14mer | 548 | 152 |
| 68 (SEQ ID NO: 7) | 5'-CTGACRTTCTCTGT-3'<br>5'-CTGACRTTCTCTGT-3'  ⎤-3'-T-5' | 14mer | 1052 | 1020 |
| 69 (SEQ ID NO: 36) | 5'-TCTGAYGTTCT-3'<br>5'-TCTGAYGTTCT-3'  ⎤-3'-T-5' | 11mer | 2050 | 2724 |
| 70 (SEQ ID NO: 24) | 5'-TCTGACRTTCT-3'<br>5'-TCTGACRTTCT-3'  ⎤-3'-T-5' | 11mer | 1780 | 1741 |
| 71 N/A | 5'-GAYGTTCT-3'<br>5'-GAYGTTCT-3'  ⎤-3'-T-5' | 8mer | 189 | 55 |
| 72 N/A | 5'-GACRTTCT-3'<br>5'-GACRTTCT-3'  ⎤-3'-T-5' | 8mer | 397 | 212 |

5'-CTGACGTTCT-3'  ⎤ $X_3$
5'-CTGACGTTCT-3'  ⎦

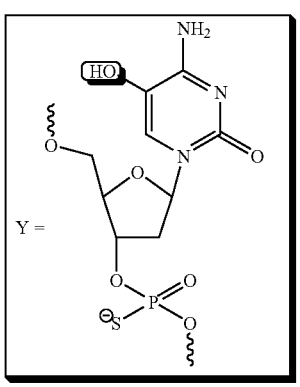

Example 6

Effect of the Linker on Immunostimulatory Activity

In order to examine the effect of the length of the linker connecting the two oligonucleotides, immunomers that contained the same oligonucleotides, but different linkers were synthesized and tested for immunostimulatory activity. The results shown in Table 12 suggest that linker length plays a role in the immunostimulatory activity of immunomers. The best immunostimulatory effect was achieved with C3- to C6-alkyl linkers or abasic linkers having interspersed phosphate charges.

TABLE 12

Immunomer Structure and Immunostimulatory Activity

| No. | Sequences and Modification (5'-3') | Oligo Length/or Each Chain | IL-12 (pg/mL) 0.3 µg/mL | IL-6 (pg/mL) 1 µg/mL |
|---|---|---|---|---|
| 4 (SEQ ID NO: 2) | 5'-CTATCTGACGTTCTCTGT-3' | 18mer | 257 | 635 |
| 73 | (SEQ ID NO: 37) 5'-CTGACGTTCT-3'⟩$X_1$ 5'-CTGACGTTCT-3'⟋ | 10mer | 697 | 1454 |
| 74 | (SEQ ID NO: 37) 5'-CTGACGTTCT-3'⟩$X_2$ 5'-CTGACGTTCT-3'⟋ | 10mer | 1162 | 669 |
| 75 | (SEQ ID NO: 37) 5'-CTGACGTTCT-3'⟩$X_3$ 5'-CTGACGTTCT-3'⟋ | 10mer | 1074 | 1375 |
| 76 | (SEQ ID NO: 37) 5'-CTGACGTTCT-3'⟩$X_4$ 5'-CTGACGTTCT-3'⟋ | 10mer | 563 | 705 |
| 77 | (SEQ ID NO: 37) 5'-CTGACGTTCT-3'⟩$X_5$ 5'-CTGACGTTCT-3'⟋ | 10mer | 264 | 543 |
| 78 | (SEQ ID NO: 37) 5'-CTGACGTTCT-3'⟩$X_6$ 5'-CTGACGTTCT-3'⟋ | 10mer | 1750 | 2258 |
| 79 | (SEQ ID NO: 37) 5'-CTGACGTTCT-3'⟩$(X_3psX_3)$ 5'-CTGACGTTCT-3'⟋ | 10mer | 2255 | 2034 |
| 80 | (SEQ ID NO: 37) 5'-CTGACGTTCT-3'⟩$(X_3psX_3psX_3)$ 5'-CTGACGTTCT-3'⟋ | 10mer | 1493 | 1197 |

TABLE 12-continued

Immunomer Structure and Immunostimulatory Activity

| No. | Sequences and Modification (5'-3') | Oligo Length/or Each Chain | IL-12 (pg/mL) 0.3 µg/mL | IL-6 (pg/mL) 1 µg/mL |
|---|---|---|---|---|
| 81 | (SEQ ID NO: 37) 5'-CTGACGTTCT-3'<br>5'-CTGACGTTCT-3' $>$ (X$_6$psX$_6$) | 10mer | 3625 | 2642 |
| 82 | (SEQ ID NO: 37)<br>5'-CTGACGTTCT-3'<br>5'-CTGACGTTCT-3' $>$ (X$_6$psX$_6$psX$_6$) | 10mer | 4248 | 2988 |
| 83 | (SEQ ID NO: 37) 5'-CTGACGTTCT-3'<br>5'-CTGACGTTCT-3' $>$ PO$_3$S | 10mer | 1241 | 1964 |

$X_1$ = structure with O at position 1, OH at position 3, O at position 2

$X_2$ = structure with O—C—C—C—O (positions 1, 2, 3)

$X_3$ = structure with O at position 1, O at position 3, positions 2 and 4

$X_4$ = O—(CH$_2$)$_{12}$—O $X_5$ = structure with O—(C)$_6$—O $X_6$ = tetrahydrofuran structure with O at positions 1, 2, 3

Example 7

Effect of Oligonucleotide Backbone on Immunostimulatory Activity

In general, immunostimulatory oligonucleotides that contain natural phosphodiester backbones are less immunostimulatory than are the same length oligonucleotides with a phosphorothioate backbones. This lower degree of immunostimulatory activity could be due in part to the rapid degradation of phosphodiester oligonucleotides under experimental conditions. Degradation of oligonucleotides is primarily the result of 3'-exonucleases, which digest the oligonucleotides from the 3' end. The immunomers of this example do not contain a free 3' end. Thus, immunomers with phosphodiester backbones should have a longer half life under experimental conditions than the corresponding monomeric oligonucleotides, and should therefore exhibit improved immunostimulatory activity. The results presented in Table 13 demonstrate this effect, with Immunomers 84 and 85 exhibiting immunostimulatory activity as determined by cytokine induction in BALB/c mouse spleen cell cultures.

TABLE 13

Immunomer Structure and Immunostimulatory Activity

| No. | Sequences and Modification (5'-3') | Oligo Length/ or each Chain | IL-12 (pg/mL) 0.3 µg/mL | IL-6 (pg/mL) 1 µg/mL |
|---|---|---|---|---|
| 4 | 5'-CTATCTGACGTTCTCTGT-3' (SEQ ID NO: 2) | 18mer | 225 | 1462 |

TABLE 13-continued

Immunomer Structure and Immunostimulatory Activity

| No. | Sequences and Modification (5'-3') | Oligo Length/ or each Chain | IL-12 (pg/mL) 0.3 µg/mL | IL-6 (pg/mL) 1 µg/mL |
|---|---|---|---|---|
| 84 (SEQ ID NO: 8) | 5'-CTGACGTTCTCTGT-3'⎤<br>⎟—3'-T-5' (PO)<br>5'-CTGACGTTCTCTGT-3"⎦ | 14mer | 1551 | 159 |
| 85 (SEQ ID NO: 8) | 5'-LLCTGACGTTCTCTGT-3'⎤<br>⎟—3'-T-5' (PO)<br>5'-LLCTGACGTTCTCTGT-3'⎦ | 14mer | 466 | 467 |

L = C3-Linker

Example 8

In vivo Anti-cancer Activity of Immunomers in Combination with Chemotherapeutic Agents PC3 cells were cultured in 90% Ham's, F12K Medium with 10% Fetal Bovine Serum (FBS), in presence of 100 U/ml Penicillin and 100 µg/ml Streptomycin to establish the Human Prostate cancer model (PC3). Male athymic nude mice, 4-6 weeks old (Frederick Cancer Research and Development Center, Frederick, Md.), were accommodated for 6 days for environmental adjustment prior to the study. Cultured PC3 cells were harvested from the monolayer cultures, washed twice with Ham's, F12K Medium (10% FBS), resuspended in FBS-free Ham's, F12K Medium: Matrigel basement membrane matrix (Becton Dickinson Labware, Bedford, Mass.) (5:1; V/V), and injected subcutaneously (5×10$^6$ cells, total volume 0.2 ml) into the left inguinal area of each of the mice. The animals were monitored by general clinical observation, body weight, and tumor growth. Tumor growth was monitored by the measurement, with calipers, of two perpendicular diameters of the implant. Tumor mass (weight in grams) was calculated by the formula, $1/2a \times b^2$, where 'a' is the long diameter (cm) and 'b' is the short diameter (cm). When the mean tumor sizes reached ~80 mg, the animals bearing human cancer xenografts were randomly divided into the treatment and control groups (5 animals/group). The control group received sterile physiological saline (0.9% NaCl) only. Immunomer 255 or 285, aseptically dissolved in physiological saline, was administered by subcutaneously injection at dose of 0.5 or 1.0 mg/kg/day, 3 doses/week. Gemcitabine HCl (Eli Lilly and Company, Indianapolis, Ind.) was given twice by intraperitoneal injection at 160 mg/kg on Day 0 and 3. The detailed treatment schedule is shown as follows.

| | |
|---|---|
| G1: | Saline |
| G2: | Gemcitabine (160 mg/kg/day, IP, Day 0 and 3) |
| G3: | 255 (1.0 mg/kg/day, SC, 3 doses/week, for 6 weeks) |
| G4: | 255 (0.5 mg/kg/day, SC, 3 doses/week, for 6 weeks) |
| G5: | 285 (1.0 mg/kg/day, SC, 3 doses/week, for 6 weeks) |
| G6: | 285 (0.5 mg/kg/day, SC, 3 doses/week, for 6 weeks) |
| G7: | 255 (0.5 mg/kg/day, SC, 3 doses/week, for 6 weeks) + Gemcitabine (160 mg/kg/day, Day 0 and 3) |
| G8: | 285 (0.5 mg/kg/day, SC, 3 doses/week, for 6 weeks) + Gemcitabine (160 mg/kg/day, Day 0 and 3) |

Figure 13:
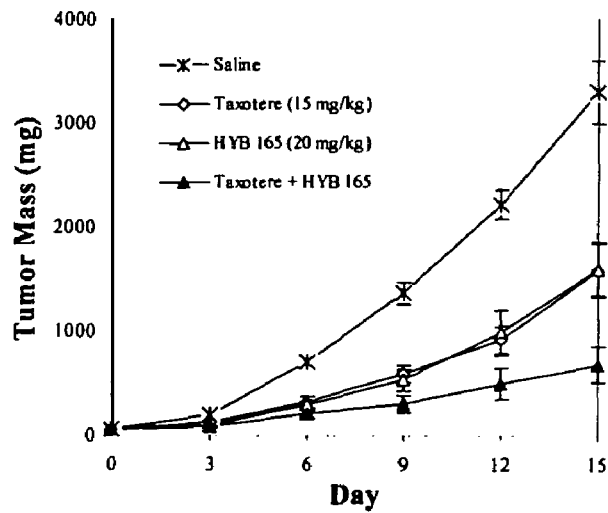
FIG. 13 shows the effect of a method according to the invention on tumor growth in a nude mouse model for prostate cancer.
Figure 13:
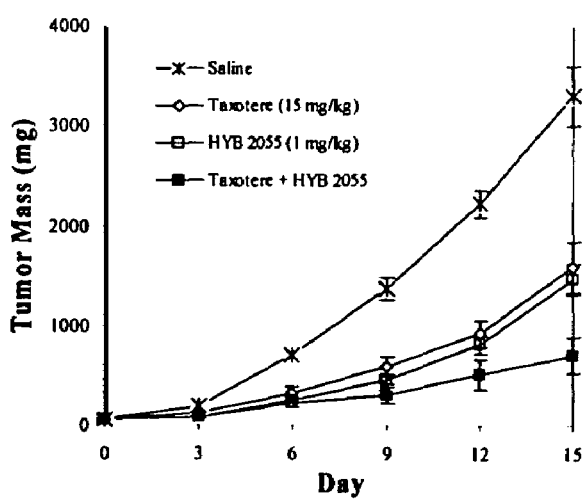
Figure 13:
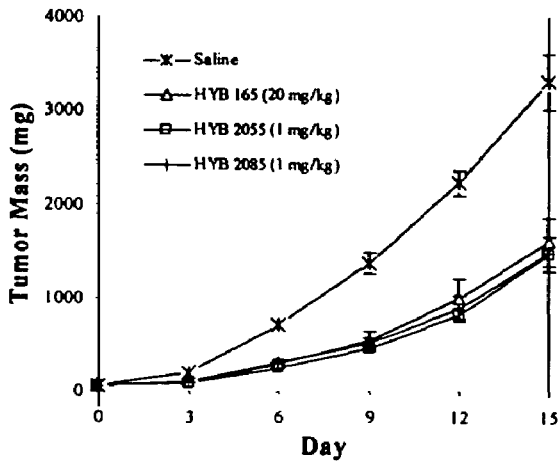

The tumor measurements after various treatments are presented in Table 14 and FIG. 13. The tumor growth in all Immunomer 255 and 285 treated animals was remarkably inhibited compared with saline control (p<0.5). There was a tendency of dose-response relationship in these treatment groups (FIG. 13). There was no significant difference between Immunomers 255 and 285 (Table 14).

TABLE 14

Tumor mass of tumor-bearing mice following treatment of 255, 285, Gemcitabine or combination therapy

| Day | Saline | SD | SE | Gemcitabine 160 mg/kg | SD | SE | 255 1 mg/kg | SD | SE | 255 0.5 mg/kg | SD | SE |
|---|---|---|---|---|---|---|---|---|---|---|---|---|
| 0 | 82.7 | 16.7 | 7.5 | 82.6 | 15.7 | 7.0 | 80.1 | 10.6 | 4.7 | 80.4 | 10.5 | 4.7 |
| 3 | 81.9 | 13.3 | 5.9 | 73.0 | 3.4 | 1.5 | 67.5 | 8.1 | 3.6 | 54.3 | 8.4 | 3.7 |
| 6 | 80.5 | 11.5 | 5.2 | 50.4 | 11.7 | 5.2 | 50.4 | 9.0 | 4.0 | 45.3 | 5.5 | 2.5 |
| 9 | 87.7 | 8.2 | 3.7 | 35.7 | 6.3 | 2.8 | 40.9 | 5.1 | 2.3 | 43.9 | 9.3 | 4.2 |
| 12 | 97.6 | 18.6 | 8.3 | 36.2 | 3.3 | 1.5 | 41.3 | 6.2 | 2.8 | 46.5 | 3.8 | 1.7 |
| 15 | 112.0 | 21.5 | 9.6 | 31.7 | 4.1 | 1.8 | 42.8 | 12.8 | 5.7 | 50.0 | 14.1 | 6.3 |
| 18 | 126.3 | 17.3 | 7.7 | 40.8 | 8.4 | 3.7 | 54.9 | 7.6 | 3.4 | 59.3 | 6.7 | 3.0 |
| 21 | 152.5 | 25.5 | 11.4 | 47.4 | 9.8 | 4.4 | 62.5 | 10.4 | 4.6 | 71.0 | 16.7 | 7.5 |
| 24 | 187.0 | 29.2 | 13.1 | 56.5 | 5.2 | 2.3 | 79.5 | 24.1 | 10.8 | 100.1 | 9.7 | 4.3 |

TABLE 14-continued

Tumor mass of tumor-bearing mice following treatment of 255, 285, Gemcitabine or combination therapy

| | | | | | | | | | | | | |
|---|---|---|---|---|---|---|---|---|---|---|---|---|
| 27 | 245.2 | 24.1 | 10.8 | 68.0 | 14.8 | 6.6 | 94.1 | 28.9 | 12.9 | 124.5 | 21.1 | 9.5 |
| 30 | 343.6 | 63.9 | 28.6 | 89.4 | 11.1 | 5.0 | 119.8 | 18.7 | 8.3 | 162.4 | 37.5 | 16.8 |
| 33 | 438.5 | 107.1 | 47.9 | 106.5 | 14.1 | 6.3 | 176.6 | 43.8 | 19.6 | 213.6 | 66.7 | 29.8 |
| 36 | 614.4 | 185.1 | 82.8 | 144.2 | 48.2 | 21.6 | 248.7 | 47.0 | 21.0 | 325.3 | 106.2 | 47.5 |
| 39 | 866.8 | 237.4 | 106.2 | 175.3 | 61.4 | 27.5 | 320.1 | 64.2 | 28.7 | 416.8 | 154.5 | 69.1 |
| 42 | 1136.9 | 205.9 | 92.1 | 269.1 | 78.8 | 35.2 | 417.8 | 78.7 | 35.2 | 546.9 | 139.1 | 62.2 |
| 45 | | | | 383.8 | 146.4 | 65.5 | 550.8 | 134.2 | 60.0 | 667.6 | 284.9 | 127.4 |
| 48 | | | | 538.6 | 260.1 | 116.3 | 736.0 | 197.3 | 88.2 | 852.8 | 399.3 | 178.6 |

| Day | 285 1 mg/kg | SD | SE | 285 0.5 mg/kg | SD | SE | 255 + GEM 0.5/160 mg/kg | SD | SE | 285 + GEM 0.5/160 mg/kg | SD | SE |
|---|---|---|---|---|---|---|---|---|---|---|---|---|
| 0 | 80.4 | 11.0 | 4.9 | 79.9 | 10.3 | 4.6 | 79.4 | 10.1 | 4.5 | 78.7 | 12.0 | 5.4 |
| 3 | 52.3 | 9.3 | 4.2 | 64.7 | 9.0 | 4.0 | 45.1 | 8.2 | 3.7 | 44.6 | 8.7 | 3.9 |
| 6 | 38.8 | 4.6 | 2.1 | 46.9 | 14.7 | 6.6 | 31.2 | 5.9 | 2.6 | 34.7 | 4.4 | 2.0 |
| 9 | 34.5 | 9.5 | 4.3 | 43.5 | 13.6 | 6.1 | 22.1 | 4.8 | 2.1 | 23.0 | 3.2 | 1.5 |
| 12 | 35.8 | 9.4 | 4.2 | 43.0 | 15.9 | 7.1 | 15.0 | 3.8 | 1.7 | 11.9 | 2.2 | 1.0 |
| 15 | 36.6 | 8.7 | 3.9 | 48.6 | 15.4 | 6.9 | 18.0 | 3.1 | 1.4 | 12.4 | 3.5 | 1.6 |
| 18 | 45.1 | 14.6 | 6.5 | 62.0 | 20.2 | 9.0 | 17.9 | 3.1 | 1.4 | 15.5 | 1.7 | 0.8 |
| 21 | 53.5 | 12.3 | 5.5 | 73.6 | 20.5 | 9.2 | 18.3 | 2.8 | 1.2 | 14.8 | 2.1 | 1.0 |
| 24 | 72.6 | 22.7 | 10.1 | 93.6 | 23.0 | 10.3 | 23.6 | 4.5 | 2.0 | 23.0 | 1.5 | 0.7 |
| 27 | 86.5 | 13.7 | 6.1 | 119.3 | 17.3 | 7.8 | 27.8 | 4.1 | 1.8 | 25.9 | 3.7 | 1.7 |
| 30 | 114.5 | 22.8 | 10.2 | 157.1 | 49.0 | 21.9 | 33.6 | 5.0 | 2.2 | 36.9 | 6.5 | 2.9 |
| 33 | 161.4 | 44.1 | 19.7 | 218.1 | 81.2 | 36.3 | 43.8 | 10.9 | 4.9 | 47.7 | 16.1 | 7.2 |
| 36 | 198.3 | 43.5 | 19.4 | 313.2 | 104.6 | 46.8 | 50.3 | 13.6 | 6.1 | 46.4 | 16.4 | 7.3 |
| 39 | 249.8 | 77.9 | 34.9 | 420.2 | 199.4 | 89.2 | 67.3 | 29.4 | 13.2 | 59.4 | 28.7 | 12.9 |
| 42 | 366.5 | 110.5 | 49.4 | 527.5 | 219.0 | 98.0 | 77.2 | 28.0 | 12.5 | 82.1 | 29.1 | 13.0 |
| 45 | 490.2 | 122.2 | 54.7 | 620.3 | 258.1 | 115.4 | 104.9 | 57.9 | 25.9 | 110.7 | 46.3 | 20.7 |
| 48 | 683.4 | 144.6 | 64.7 | 759.1 | 223.0 | 99.7 | 128.2 | 77.7 | 34.7 | 133.4 | 62.6 | 28.0 |
| 51 | | | | | | | 177.9 | 109.6 | 49.0 | 177.3 | 68.0 | 30.4 |
| 54 | | | | | | | 233.1 | 143.5 | 64.2 | 224.0 | 79.8 | 35.7 |
| 57 | | | | | | | 297.7 | 190.7 | 85.3 | 289.7 | 121.9 | 54.5 |

Figure 14:
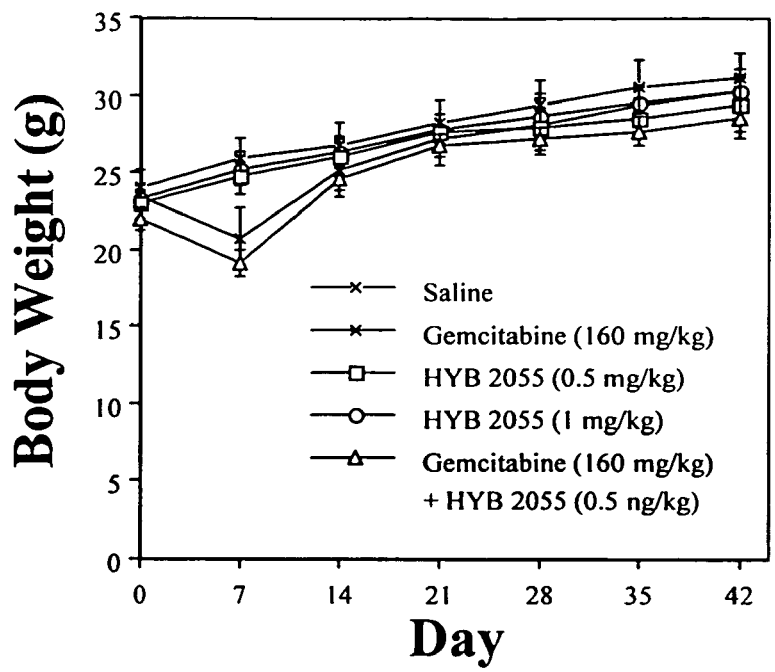
FIG. 14 shows the effect of a method according to the invention on body weight of the mice used in the study.
Figure 14:
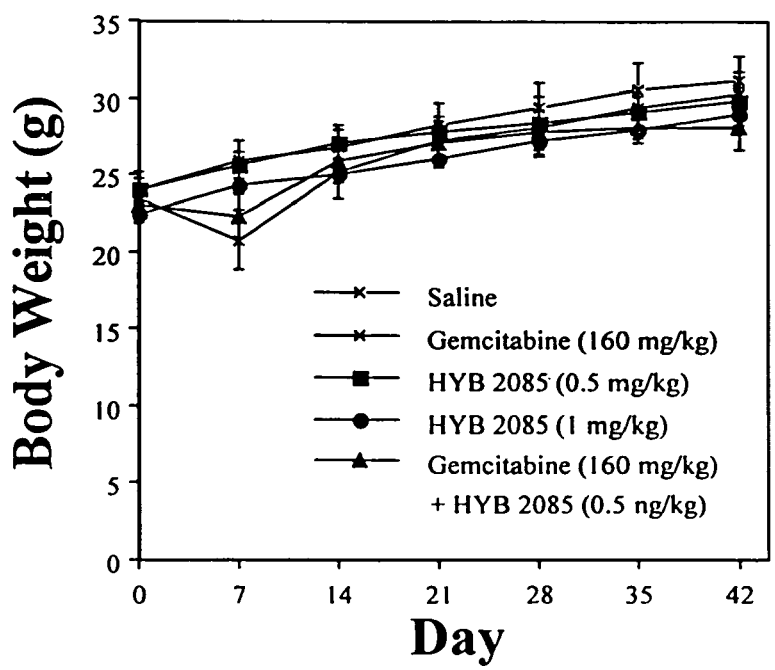

The body weight measurements after treatments at various times are presented in Table 15 and FIG. 14. There was no significant difference in body weight gains among Immunomer 255 or 285 alone compared with controls. Gemcitabine treated animals had body weight loss in the first week and recovered in a week afterwards. Combination with Immunomer 255 or 285 did not change the side effect profiles of Gemcitabine. No other clinical abnormality or death was observed in all the groups.

In summary, Immunomers 255 and 285 significantly inhibited tumor growth in nude mice bearing human prostate cancer PC3 xenografts with no significant side effects. When Immunomer 255 or 285 was given in combination with Gemcitabine, each compound significantly increased the therapeutic effect of Gemcitabine without changes in side effect profiles. In addition, there was a tendency in dose dependent response of Immunomer 255 or 285 treatment.

TABLE 15

Body weights of tumor-bearing mice following treatment of 255, or saline.

| Day | Saline | SD | SE | Gemcitabine 160 mg/kg | SD | SE | 255 1 mg/kg | SD | SE | 255 0.5 mg/kg | SD | SE |
|---|---|---|---|---|---|---|---|---|---|---|---|---|
| 0 | 24.1 | 2.5 | 1.1 | 23.5 | 0.9 | 0.4 | 23.2 | 1.4 | 0.6 | 23.0 | 2.4 | 1.1 |
| 7 | 25.8 | 3.0 | 1.3 | 20.7 | 4.4 | 2.0 | 25.2 | 2.4 | 1.1 | 24.8 | 2.8 | 1.2 |
| 14 | 26.8 | 3.2 | 1.4 | 25.2 | 4.0 | 1.8 | 26.3 | 2.0 | 0.9 | 26.0 | 2.9 | 1.3 |
| 21 | 28.2 | 3.3 | 1.5 | 27.1 | 3.9 | 1.7 | 27.8 | 2.0 | 0.9 | 27.6 | 2.8 | 1.2 |
| 28 | 29.4 | 3.5 | 1.6 | 28.1 | 4.3 | 1.9 | 28.6 | 2.6 | 1.1 | 28.0 | 2.7 | 1.2 |
| 35 | 30.6 | 3.7 | 1.6 | 29.4 | 2.9 | 1.3 | 29.5 | 2.3 | 1.0 | 28.6 | 2.8 | 1.3 |
| 42 | 31.1 | 3.7 | 1.7 | 30.3 | 3.0 | 1.4 | 30.2 | 2.3 | 1.0 | 29.4 | 3.9 | 1.7 |

| Day | 285 1 mg/kg | SD | SE | 285 0.5 mg/kg | SD | SE | 255 + GEM 0.5/160 mg/kg | SD | SE | 285 + GEM 0.5/160 mg/kg | SD | SE |
|---|---|---|---|---|---|---|---|---|---|---|---|---|
| 0 | 22.5 | 1.3 | 0.6 | 24.1 | 1.6 | 0.7 | 21.9 | 1.7 | 0.7 | 23.0 | 0.8 | 0.4 |
| 7 | 24.3 | 0.9 | 0.4 | 25.6 | 2.0 | 0.9 | 19.1 | 2.0 | 0.9 | 22.3 | 3.3 | 1.5 |
| 14 | 25.1 | 1.3 | 0.6 | 27.0 | 2.1 | 0.9 | 24.6 | 1.6 | 0.7 | 25.9 | 2.7 | 1.2 |
| 21 | 26.1 | 1.3 | 0.6 | 27.8 | 1.5 | 0.7 | 26.8 | 1.6 | 0.7 | 27.1 | 2.6 | 1.2 |
| 28 | 27.2 | 1.5 | 0.7 | 28.3 | 2.2 | 1.0 | 27.2 | 1.6 | 0.7 | 27.7 | 3.2 | 1.4 |
| 35 | 28.0 | 1.4 | 0.6 | 29.1 | 2.3 | 1.0 | 27.7 | 2.1 | 1.0 | 28.0 | 2.4 | 1.1 |
| 42 | 28.9 | 1.5 | 0.7 | 29.8 | 2.2 | 1.0 | 28.4 | 2.8 | 1.2 | 28.1 | 3.4 | 1.5 |

Example 9

In vivo Anti-cancer Activity of Immunomers in Combination with Chemotherapeutic Agents The experiment of Example 8 was repeated using taxotere instead of Gemcitabine. Taxotere was administered on days 0 and 7. Immunomer 165 was administered 5 days per week. Immunomers 255 and 285 were administered on days 0, 2, 4, 7, 9 and 11. The results are shown in Table 16 below. These results clearly demonstrate synergy between the immunomers and taxotere.

For the analysis of serum antibodies, 96 well plates were incubated at room temperature for 3 hours with β-gal protein (Calbiochem Novabiochem, Pasadena, Calif.) at 2 μg/ml in phosphate buffered saline (PBS). The solid phase was incubated overnight at 4° C. with normal mouse serum (NMS) or antiserum, or β-gal specific monoclonal Ab (Calbiochem Novabiochem, Pasadena, Calif.) followed by an incubation with horseradish peroxidase (HRP)-conjugated antibodies specific for mouse IgG (H+L). For isotype analysis, HRP-labelled goat anti-mouse IgG1 and IgG2a (Southern Biotechnology, Birmingham, Ala.) were used. The binding of antibodies was measured as absorbance at 405 nm after reaction of the immune complexes with ABTS substrate (Zymed, San Francisco, Calif.).

TABLE 16

In vivo anti-cancer activity of immunomers in combination with other chemotherapeutic agents

| Day | Saline | SD | SE | Taxotere (15 mg/kg) | SD | SE | 165 (20 mg/kg) | SD | SE | 255 (1 mg/kg) | SD | SE |
|---|---|---|---|---|---|---|---|---|---|---|---|---|
| 0.00 | 56.93 | 7.92 | 3.54 | 56.64 | 7.94 | 3.55 | 57.93 | 5.56 | 2.49 | 56.74 | 7.79 | 3.48 |
| 3.00 | 196.42 | 22.48 | 10.05 | 128.51 | 20.83 | 9.32 | 95.79 | 16.04 | 7.18 | 87.12 | 6.64 | 2.97 |
| 6.00 | 708.85 | 32.64 | 14.60 | 320.63 | 136.80 | 61.18 | 285.71 | 68.70 | 30.72 | 250.36 | 52.58 | 23.51 |
| 9.00 | 1370.95 | 239.99 | 107.33 | 598.69 | 196.60 | 87.92 | 534.93 | 225.19 | 100.71 | 450.46 | 92.25 | 41.26 |
| 12.00 | 2222.96 | 300.65 | 134.45 | 924.91 | 297.89 | 133.22 | 994.10 | 474.89 | 212.38 | 814.21 | 197.16 | 88.17 |
| 15.00 | 3303.04 | 672.86 | 300.91 | 1589.08 | 578.38 | 258.66 | 1601.73 | 576.19 | 257.68 | 1465.87 | 348.37 | 155.80 |

| Day | Saline | Taxotere + 165 | SD | SE | Taxotere + 255 (**mg/kg) | SD | SE | 285 (1 mg/kg) | SD | SE |
|---|---|---|---|---|---|---|---|---|---|---|
| 0.00 | 56.93 | 55.51 | 9.55 | 4.27 | 56.59 | 8.91 | 3.99 | 55.28 | 10.89 | 4.87 |
| 3.00 | 196.42 | 78.47 | 21.79 | 9.74 | 80.14 | 21.59 | 9.65 | 91.01 | 23.60 | 10.55 |
| 6.00 | 708.85 | 211.52 | 88.59 | 39.62 | 216.85 | 89.40 | 39.98 | 303.00 | 61.33 | 27.43 |
| 9.00 | 1370.95 | 302.66 | 178.36 | 79.76 | 307.53 | 184.05 | 82.31 | 512.30 | 110.16 | 49.26 |
| 12.00 | 2222.96 | 496.20 | 342.69 | 153.25 | 510.18 | 351.16 | 157.04 | 884.12 | 308.22 | 137.84 |
| 15.00 | 3303.04 | 686.47 | 385.97 | 172.61 | 703.50 | 394.65 | 176.49 | 1479.21 | 416.64 | 186.33 |

Example 10

IMO compounds as shown in FIG. 15 and a non-CpG DNA: (5'-CTATCTCACCTTCTCTGT-3', SEQ ID NO: 38) were synthesized, purified, and analyzed as described above.

Female BALB/c (H-$2^d$), C57BL/6, and IL-6 and IL-12 knockout (ko) (both ko on a C57BL/6 background) mice 5-8 weeks of age, were purchased from Jackson Laboratory (Bar Harbor, Me.). CT26.WT (ATCC, Rockville, Md.) is a carcinogen-induced BALB/c undifferentiated colon carcinoma. CT26.CL25 (ATCC, Rockville, Md.) is a subclone of CT26.WT that has been transduced with *Escherichia coli* β-gal gene. 4T1 is a mammary adenocarcinoma cell line in BALB/c mice. B16.F0 is a C57BL/6 derived melanoma (ATCC). CT26.WT and 4T1 cells were cultured in RPMI 1640, 10% heat-inactivated fetal bovine serum (FBS, Atlas Biologicals, Fort Colins, Colo.), 2 mM L-glutamine, 100 μg/ml streptomycin, 100 U/ml penicillin (Mediatech, Va.). CT26.CL25 is maintained in the same medium plus 400 μg/ml G418 sulfate (Life Technologies, Grand Island, N.Y.). B16.F0 cells were grown in DMEM containing 10% FBS and antibiotics.

To assess serum cytokine levels, BALB/c mice (n=5) were injected intraperitoneally (i.p), subcutaneously (s.c) or intramuscularly (i.m) with IMO compounds at 10 mg/kg (single dose). Sera was collected by retro-orbital bleeding at 4 hrs of IMO administration and determined IL-112 and IL-6 by sandwich ELISA. Cytokine antibodies and standards were purchased from PharMingen (San Diego, Calif.).

For subcutaneous solid tumor models, $10^6$ CT26.CL25 cells/mouse or $5 \times 10^5$ B16.F0 cells/mouse in 100 μl of PBS were implanted into BALB/c or C57BL/6 mice in the lower right flank. The tumor size reached to 50 to 200 mg on day 6 for CT26.CL25 and on day 8 for B16.F0 post tumor inoculation. The tumor bearing mice were then treated with peritumoral injection of IMO compounds or non-CpG DNA control at a dose of 1 mg/kg every other day for 10 times. Tumor growth was recorded with the use of calipers, by measuring the long and short diameters of the tumor. Tumor volumes were measured with a caliper and the formula (0.5×length× width$^2$) was applied to determine tumor growth kinetics.

For peritoneal disseminated tumor model, $3 \times 10^5$ CT26.WT or CT26.CL25 cells and $5 \times 10^4$ B16.F0 cells were injected i.p to BALB/c or C57BL/6 mice respectively. IMO compounds or non-CpG DNA (2.5 mg/kg) were administrated i.p. twice per week starting on day 1 for a total of 5 times. Mice were checked daily for tumor growth and for survival. Each dose group had 6 to 10 mice.

For the 4T1 tumor models, $5 \times 10^5$ cells/mouse in. 100 μl PBS were implanted into BALB/c mice in the lower right flank. On day 5 when the average tumor size reached 50 mm$^2$, the mice were given i.p injections of 30 mg/kg doxorubicin (Bedford lab, Bedford, Ohio) for three times on days 5, 6 and 7. IMO 2 (1 mg/kg) dissolved in 100 μl PBS was administrated by peritumoral injection at twice a week interval for a total of six times.

For B16.F0 melanoma tumor, C57BL/6 mice were injected i.p with $5 \times 10^4$ cells/mouse in 100 μl PBS on day 0. The mice were treated on day 2 with one i.p injection of 20 mg/kg docetaxel (Aventis, Bridgewater, N.J.) and then given i.p injections of 2.5 mg/kg IMO 2 on days 3, 6, 9, 12 and 15.

Long term survivors (n=5) of IMO compound treated mice with CT26.WT or CT26.CL25 peritoneal tumor were rechallenged i.p. or i.v. with 5×10$^5$ of the parental tumor cells without any further treatment. To evaluate the specificity of the IMO induced antitumor response in tumor bearing mice, these long term survivors (n=5) were also rechallenged with syngeneic, non-organ-related mammary tumor 4T1 (5×10$^5$). For i.v. rechallenged groups, mice were sacrificed on day 13, lungs were harvested and lung metastases were counted.

To study adoptive immune cell transfer, BALB/c mice were adoptively i.p. transferred with 5×10$^6$ of syngeneic splenocytes either from naïve BALB/c mice or from IMO treated long term survivors bearing CT26.WT or CT26.CL25, the mice (5/group) were then cross challenged i.p. with 3×10$^5$ CT26.WT, CT26.CL25 or 4T1 cells on day 3.

To determine T cell responses, two or three mice from each group were sacrificed at day 26 after s.c. tumor implantation or day 21 after i.p. tumor inoculation, pooled T cells from splenocytes in each group were purified using T cell enrichment columns (R&D systems, Minneapolis, Minn.). Purified T cells (2.5×10$^5$) were stimulated with 2.5×10$^5$ mitomycin C-(50 µg/ml, Sigma, St. Louis, Mo.) treated β-gal or OVA peptide-pulsed syngeneic spleen cells for 24 hrs. T cells specifically responding to H-2$^d$ restricted, antigen specific (β-gal$_{876}$-884) restimulation were then determined by interferon-gamma (IFN-γ) and IL4 ELISPOT analysis according to the manufacturer's directions (R&D Systems). Spots were enumerated electronically (Zellnet, New York, N.Y.).

Example 11

Serum Cytokine Secretion Profiles of IMO Compounds

Figure 16:
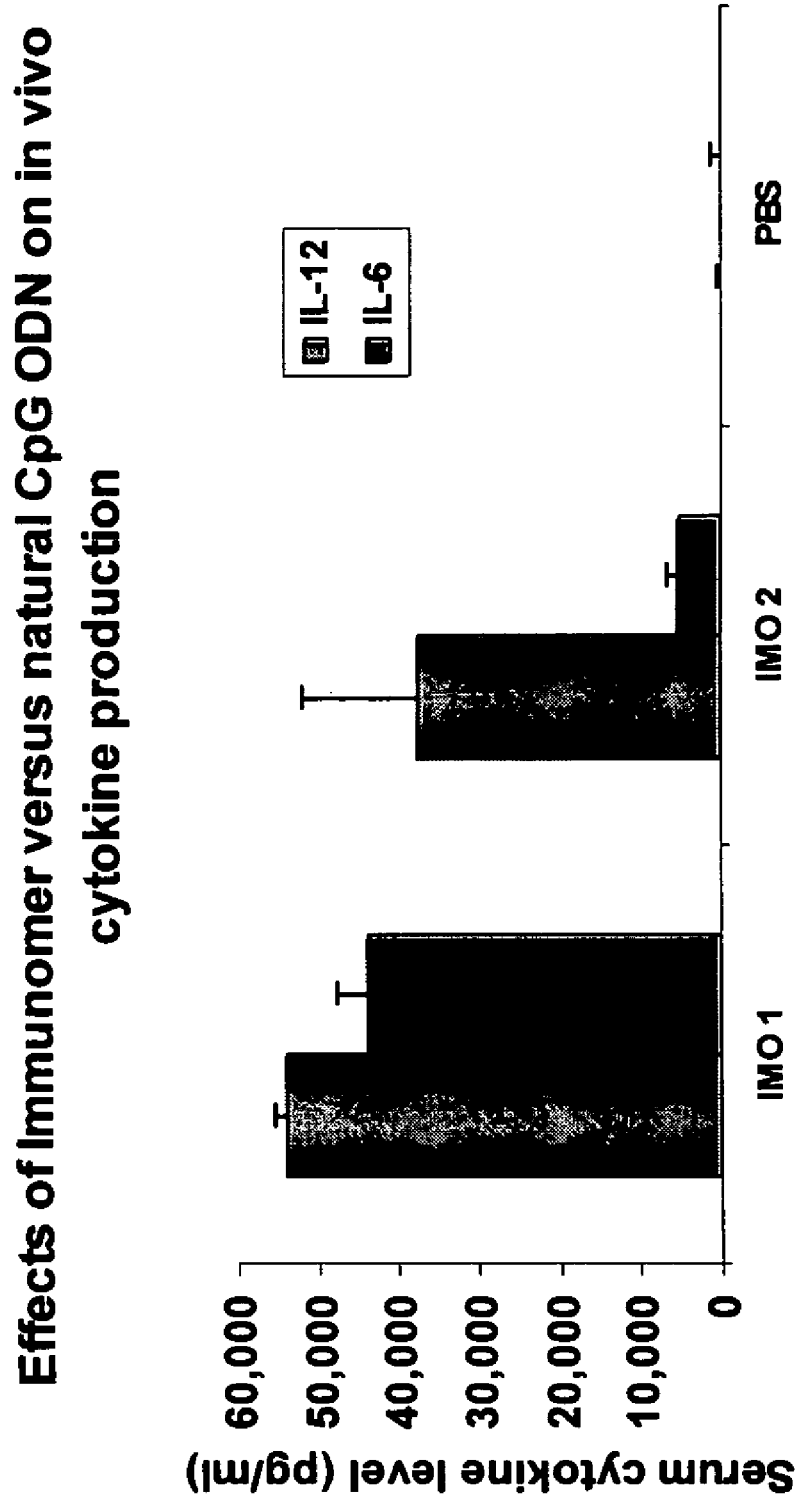
FIG. 16 shows in vitro cytokine induction profiles of IMO compounds.

IMOs 1 and 2 induce strong IL-12 secretion, while IMO 2 induced lower IL-6 production in vitro (FIG. 16). To evaluate the immunopharmacological effects in vivo, IMO compounds, CpG immunomers, and non-CpG oligos were administered to BALB/c mice i.p, s.c or i.m at a dose of 10 mg/kg and their serum was evaluated for IL-12 and IL-6 after 4 hrs. Both IMO compounds induced strong serum IL-12 secretion compared with a conventional CpG oligo (Table 17). IMO 2 containing a synthetic CpR motif, however, induced a significantly lower serum IL-6 in all three routes of administration (Table 17) further confirming our earlier in vitro studies. The control non-CpG DNA showed insignificant IL-12 and IL-6 induction.

Example 12

IMO Compounds Show Potent Antitumor Activity in Murine Colon Carcinoma Model

Figure 17:
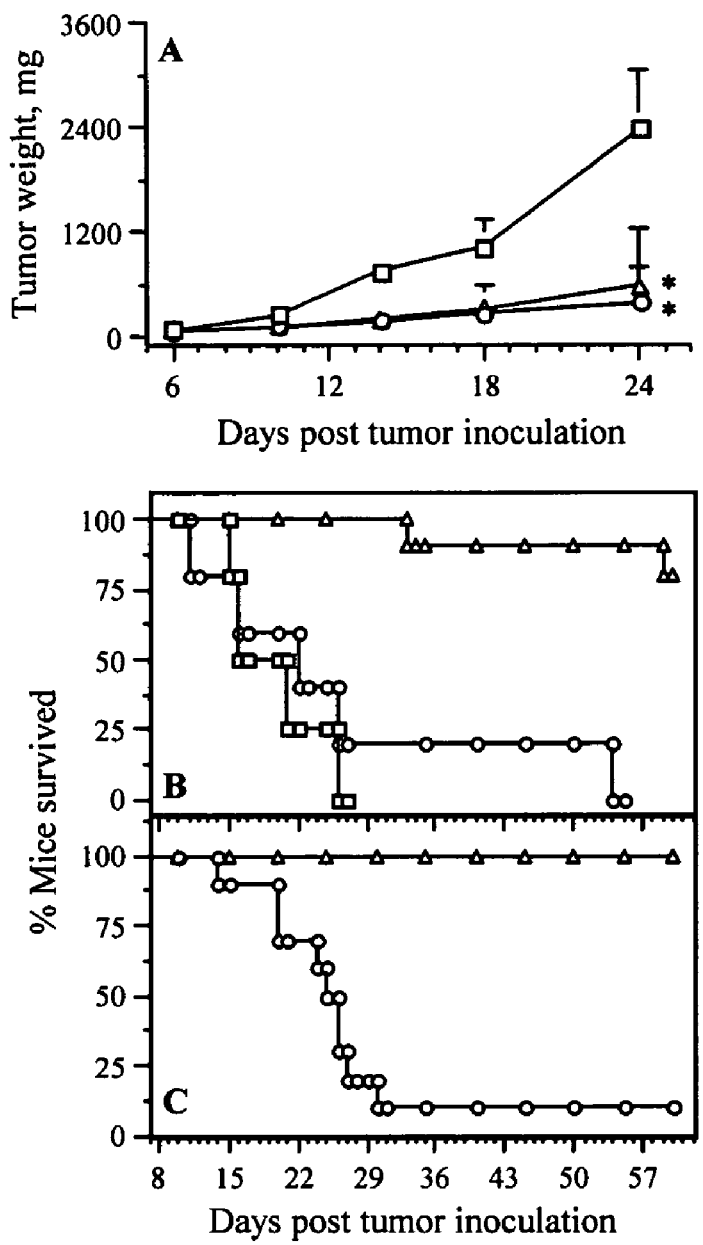
FIG. 17. (A) Antitumor activity of IMO compounds against CT26.CL25 colon tumor in BALB/c mice. IMO 1 (circles), IMO 2 (triangles) or control non-CpG DNA (squares). *$p<0.001$ compared with non-CpG DNA control group. Plots showing the survival of (B) CT26.WT or (C) CT26.CL25 tumor bearing BALB/c mice in different treatment groups. PBS (squares) or control non-CpG DNA (circles) or IMO 2 (triangles)

The antitumor activity of IMO compounds in a murine colon carcinoma CT26.CL25 model was evaluated. BALB/c mice bearing CT26.CL25 subcutaneous solid tumors were treated with 1 mg/kg IMO compounds by peritumoral administration every other day for 10 times starting on day 6 following tumor inoculation. Treatment with IMO compounds resulted in complete rejection or strong inhibition of tumor growth in up to 75% of animals (FIG. 17A). An average tumor growth inhibition of 72% and 85% was observed in mice treated with IMOs 1 and 2, respectively, on day 24 compared with non-CpG DNA treated mice. Furthermore, peritoneal administration of IMO 2 at a dose of 1 mg/kg to mice bearing peritoneal disseminated ascites CT26.WT (FIG. 17B) and CT26.CL25 (FIG. 17C) resulted in a marked increase of mice survival.

Example 13

Levels of Circulating β-gal-specific IgG1 and IgG2a Subclasses

Figure 18:
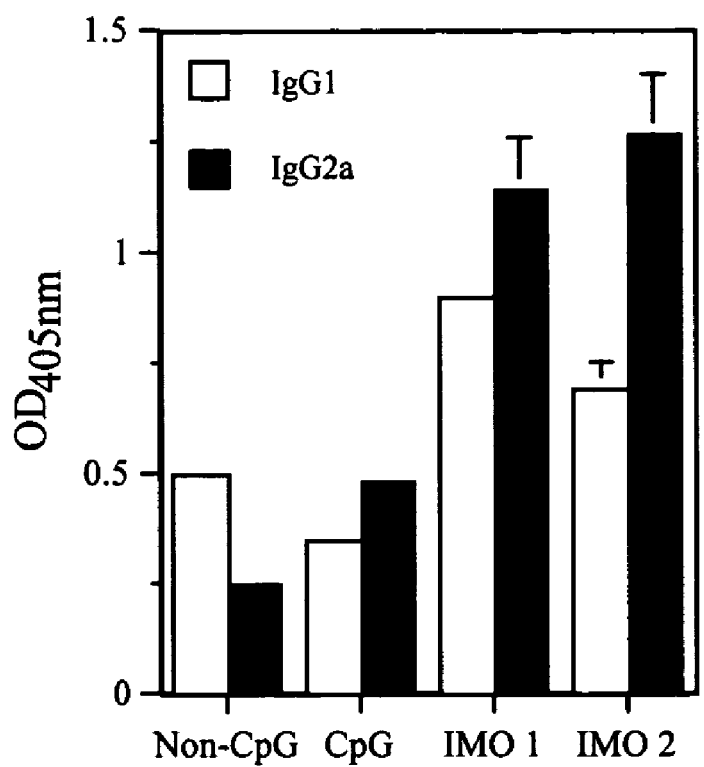
FIG. 18. Levels of serum β-gal-specific IgG 1 (open bars) and IgG2a (filled bars) in CT26.CL25 tumor bearing BALB/c mice on day 24.

The serum of CT26.CL25 tumor bearing mice following treatment with IMO compounds for β-gal-specific IgG 1 and IgG2a antibody levels was analyzed. The mice treated with IMO compounds showed over 5-fold increase (OD units) in anti-β-gal-specific IgG2a levels (FIG. 18). The treatment with a conventional CpG DNA resulted in only about a 2-fold increase in β-gal-specific IgG2a levels. In contrast, only a moderate 0.5 to 2-fold increase in β-gal-specific IgG1 levels was observed (FIG. 18).

Example 14

IMO Compounds Induce Tumor Specific CTL Responses

Figure 19:
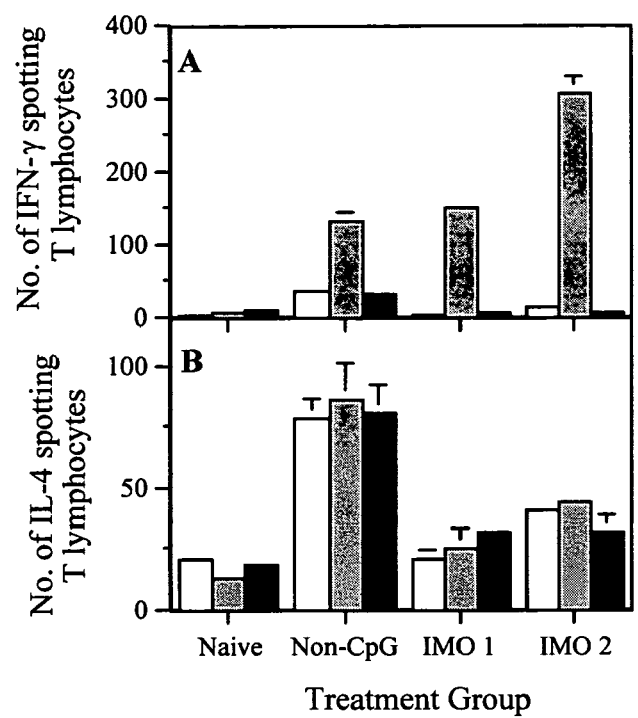
FIG. 19. (A) IFN-γ and (B) IL4 secreting T-lymphocytes in total T cells ($10^6$) isolated from the spleens of CT26.CL25 colon tumor bearing mice on day 24 in various treatment groups. PBS (open bars), β-gal (shaded bars), or OVA peptide (black bars).

To examine if IMO treatment of tumor bearing mice resulted in tumor specific CTL responses, T cells purified from splenocytes obtained from mice bearing CT26.CL25 tumor in different treatment groups were stimulated with mitomycin C-treated β-gal or OVA peptide-pulsed syngeneic spleen cells for 24 hrs. A significantly higher tumor specific CTL response to H-2$^d$ restricted (β-gal $_{876-884}$) antigen was found in mice treated with IMO compounds and CpG DNA than in mice treated with a control non-CpG DNA as determined by higher IFN-γ induction (FIG. 19A), but not IL-4 (FIG. 19B).

TABLE 17

In vivo cytokine induction$^a$ by IMO compounds administered by different routes.

| Oligo | Intraperitoneal (i.p) | | Intramuscular (i.m) | | Subcutaneous (s.c) | |
|---|---|---|---|---|---|---|
| | IL-12 | IL-6 | IL-12 | IL-6 | IL-12 | IL-6 |
| CpG DNA | 36.0 ± 0.5 | 1.1 ± 0.2 | 62.7 ± 6.4 | 0.6 ± 0.07 | 48.6 ± 6.9 | 0.3 ± 0.03 |
| IMO 1 | 59.0 ± 11 | 5.9 ± 0.2 | 109.3 ± 25 | 5.8 ± 0.5 | 98.3 ± 15 | 4.3 ± 0.3 |
| IMO 2 | 51.7 ± 0.9 | 2.5 ± 0.2 | 87.9 ± 3.2 | 1.2 ± 0.1 | 136.9 ± 17 | 2.3 ± 0.4 |
| Non-CpG | 0.86 ± 0.5 | 0.7 ± 0.3 | 1.6 ± 0.07 | Nd | 1.7 ± 0.04 | Nd |

$^a$The values shown are averages in ng/mL ± SD of three individual mouse;
nd—not detectable.

Example 15

Persistent Antitumor Memory Following IMO Treatment

Figure 20:
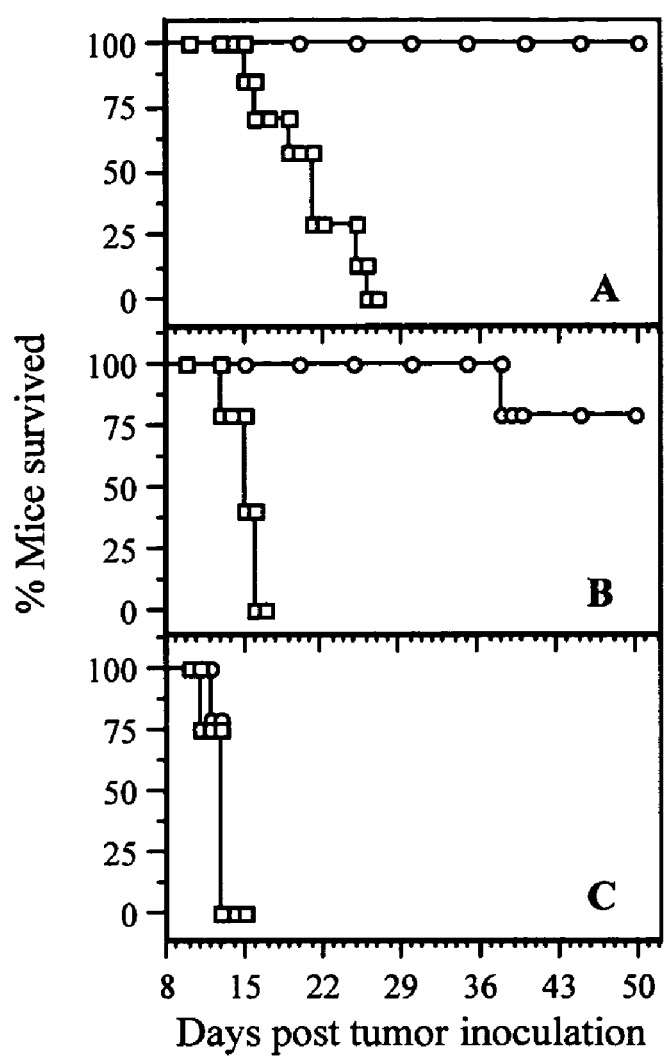
FIG. 20. Persistent antitumor memory following IMO treatment. Survival plots of long term survivors of IMO treated CT26.CL25 peritoneal tumor bearing mice rechallenged with (A) CT26.WT colon, (B) CT26.CL25 colon, or (C) 4T1 mammary carcinoma cells. IMO 2 (circles) or naive mice that were not treated with IMO motifs (squares).

To study whether the IMO treatment would also induce tumor-specific adaptive immune response, mice that had been cleared of CT26.CL25 peritoneal tumor by IMO treatment were rechallenged. Mice previously treated with IMO 2 rejected i.p rechallenge with CT26.WT and CT26.CL25 tumors (FIGS. 20A and B). The mice that survived from peritoneal injected tumor after IMO 2 treatment were also able to reject pulmonary metastases of the same tumor after i.v. inoculation (data not shown). Similar results were found in CT26.WT tumor model experiments rechallenged with CT26.WT or CT26.CL25 cells (data not shown). These data indicate that the mice treated with IMO 2 developed adaptive immune response not only against model tumor antigen β-gal, but also against parent tumor (CT26) antigens. However, such an immune memory was tumor specific and the same mice were not protected from syngeneic, non-organ-related 4T1 mammary carcinoma challenge (FIG. 20C).

Example 16

Figure 21:
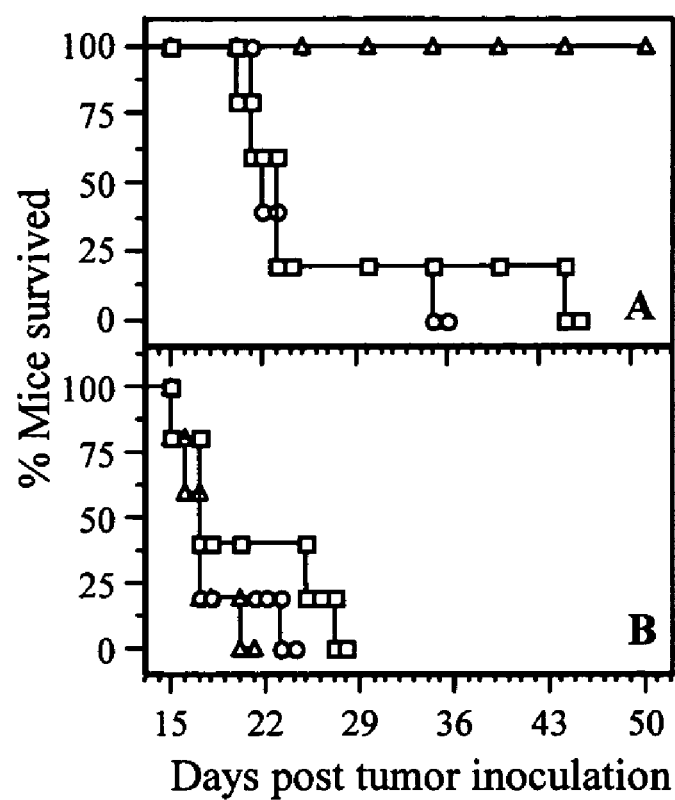
FIG. 21. Naïve mice develop specific antitumor protection following adoptive transfer of immune cells from tumor bearing mice that were treated with IMO compounds. (A) Survival of the mice to parental CT26.CL25 tumor cell challenge following adoptive transfer of the immune cells obtained from mice treated with IMO 2 (triangle) or naïve mice (circles). (B) Survival of the mice to 4T1 breast cancer cell challenge following adoptive transfer of the immune cells obtained from mice treated with IMO 2 (triangle) or naïve mice (circles). Mice injected with PBS and challenged with CT26.CL25 cells as control are shown in squares in both the panels.

Naïve Mice Develop Antitumor Protection Following Adoptive Transfer of Immune Cells from IMO Treated Mice Consistent with the concept that IMO 2 treatment induced specific antitumor immunity, splenocytes from the mice that rejected CT26.CL25 tumor after IMO treatment were transferred to naïve mice, and these mice were challenged with CT26.CL25 or 4T1 tumor cells. Splenocytes from IMO 2 treated mice, but not from naïve mice, were protective against a lethal tumor challenge with CT26.CL25 tumor cells (FIG. 21A). As in the case of tumor rechallenge experiment, this protection was tumor specific and did not extend to 4T1 tumor cell challenge (FIG. 21B).

Example 17

Figure 22:
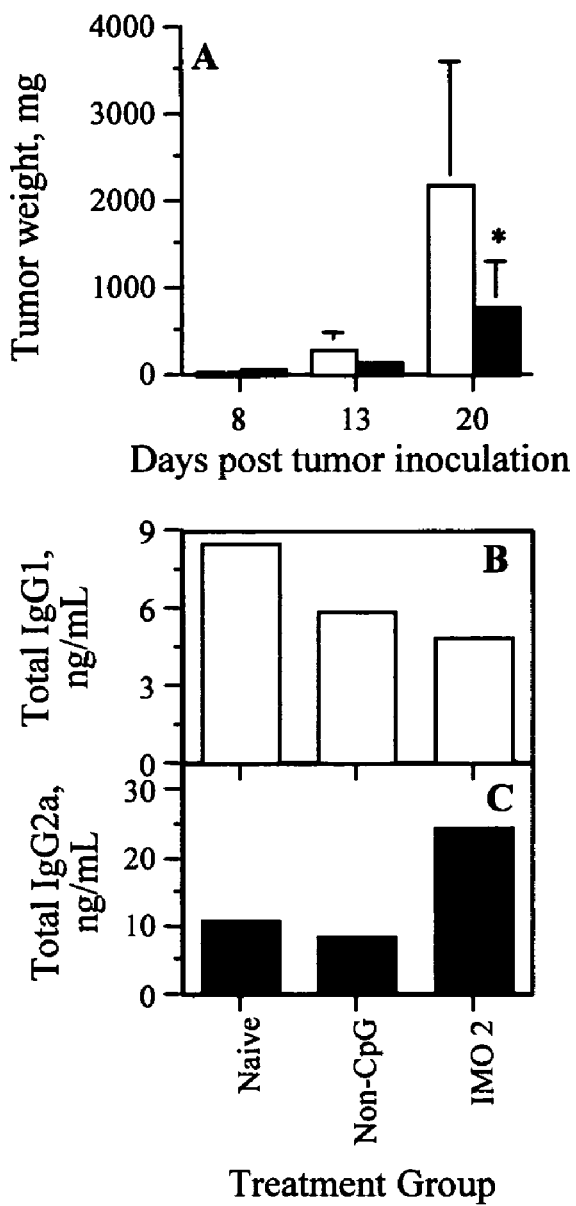
FIG. 22. (A) Antitumor activity of IMO compounds against B 16.F0 melanoma in C57BL/6 mice. IMO 2 (filled bars) or control non-CpG DNA (open bars)*p<0.0183 compared with non-CpG DNA control group. Total serum (B) IgG1 and (C) IgG2a antibody subclasses in B 16.F0 tumor bearing C57BL/6 mice on day 22 following treatment with IMO 2 or control non-CpG DNA.

IMO 2 Shows Potent Antitumor Activity and Induces IgG2a Antibody Production in Murine Melanoma Model IMO 2 was further tested for its antitumor activity in mice bearing B 16.F0 murine melanoma. C57BL/6 mice bearing B16.F0 melanoma were treated with 1 mg/kg IMO 2 by peritumoral administration every other day for 10 times starting on day 8 following tumor inoculation. As shown in FIG. 22A, IMO 2 caused a tumor growth inhibition of 71% in C57BL/6 mice bearing subcutaneous B16.F0 melanoma. IMO 1 treatment also resulted in similar levels of tumor inhibition as that of IMO 2 (data not shown).

As in the case of CT26.CL25 colon carcinoma, treatment of mice bearing B 16.F0 tumor with IMO 2 resulted in a significant increase in total circulating serum IgG2a with a decrease or no change in total IgG1 levels compared with control non-CpG DNA treated mice (FIGS. 22B and C). These results suggest the potent Th1 type immune responses in mice bearing B16.F0 melanoma following IMO treatment.

Example 18

Figure 23:
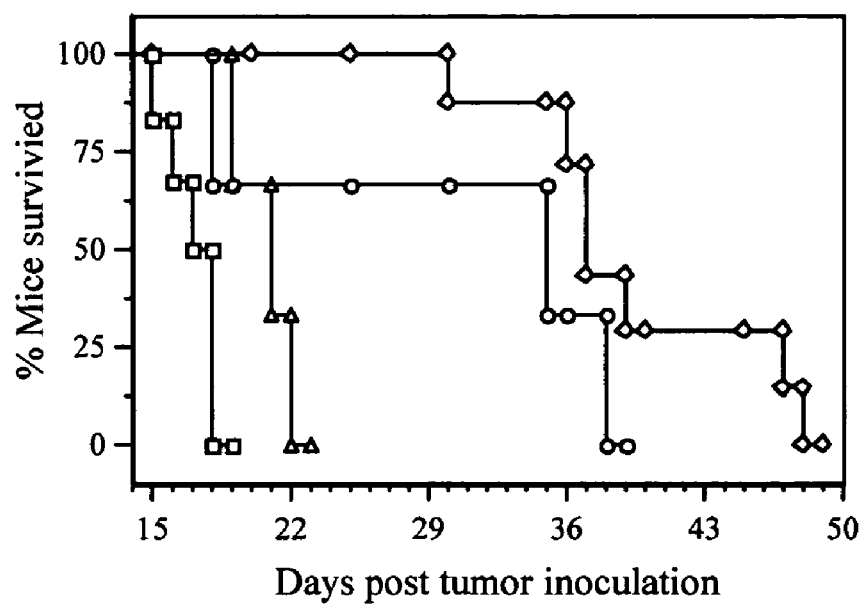
FIG. 23. Effect of IMO 2 on survival of B16.F0 melanoma bearing wt, IL-6 ko, and IL-12 ko C57BL/6 mice. Non-CpG DNA to wild-type (wt) (squares) and IMO 2 to wt (diamonds), IL-6 knockout (ko) (circles) and IL-12 ko (triangles).

IMO Induced Th1 Type Responses are Essential for Antitumor Protection in Mice Bearing B16.F0 Melanoma The data shown above including increases in IgG2a levels and tumor antigen specific CTL responses indicated a clear shift towards a Th 1-dominated responses following IMO treatment in colon carcinoma model. The antitumor effects of IMO compounds in wild-type (wt), IL-12 ko, and IL-6 ko C57BL/6 mice bearing B16 melanoma were examined. Treatment of wt and IL-6 ko C57BL/6 mice bearing B16.F0 tumor with IMO 2 resulted in a significant reduction in tumor growth (FIG. 23). However, IMO treatment had an insignificant effect on IL-12 ko mice bearing the same tumor, suggesting that IL-12 is required for IMO induced antitumor activity (FIG. 23).

Example 19

Synergy of Combination Treatment of Conventional Chemotherapeutic Agents and IMO Compounds.

Figure 24:
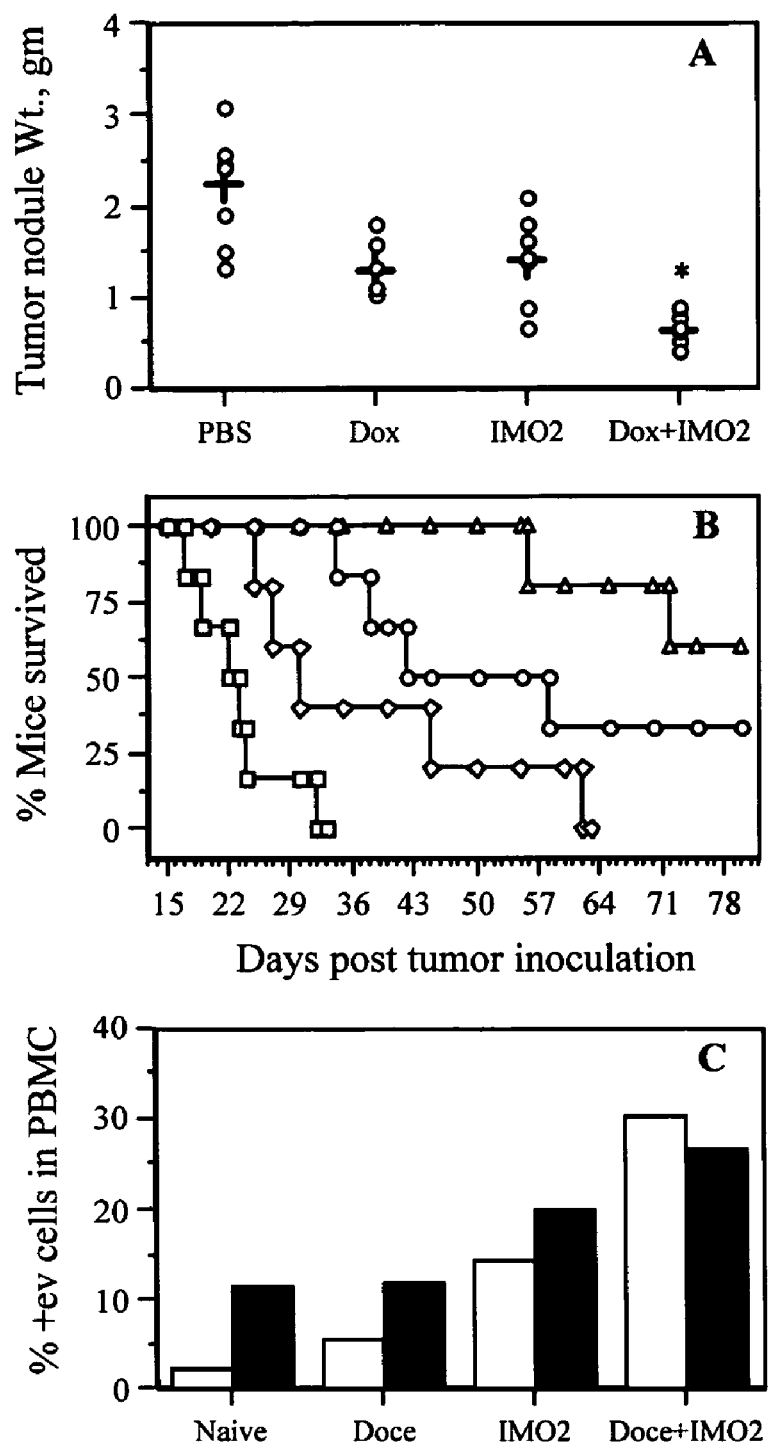
FIG. 24. Synergistic antitumor activity of the combination of conventional chemotherapy and IMO immunotherapy. (A) Growth inhibition of 4T1 breast tumor in BALB/c mice in various treatment groups. Each circle represents data of a single animal and +indicates average. *p=0.0004 compared with PBS control group. (B) Survival plots of peritoneal disseminated B 16.F0 melanoma bearing C57BL/6 mice in various treatment groups. PBS (squares), docetaxel (20 mg/kg, i.p) single dose on day 2 (diamonds), IMO 2 (2.5 mg/kg, i.p, on days 3, 6, 9, 12 and 15) (circles) or combination of docetaxel and IMO 2 at the same dose and schedule as in monotherapy (triangles). (C) Activation of CD69+ and CD86+cells in C57BL/6 mice treated with PBS, docetaxel (Doce; 30 mg/kg, i.p, on days 1 and 3), IMO 2 (5 mg/kg, i.p, on days 1, 3, 5, and 7) or docetaxel (Doce) and IMO 2. CD69+(open bars) and CD86+(filled bars)

Synergistic effects between chemotherapeutic agents and IMO compounds in mice bearing B16.F0 ascites tumors or 4T1 subcutaneous solid tumors were examined. Peritumoral injection of IMO 2 and systemic administration of doxorubicin alone gave strong inhibition of 4T1 tumor growth (FIG. 24A). In combination, the two treatments were even more potent (FIG. 24A). The combination treatment of docetaxel and IMO 2 also showed significant synergy against peritoneal disseminated B 16.F0 melanoma resulting in enhanced survival of mice over those treated with either agent alone (FIG. 24B).

The effects of docetaxel and IMO 2 treatment on immune cell activation were tested by determining the population changes of CD69+ and CD86+cells in peripheral blood. Mice treated with IMO 2 showed significant increase in the percentage of CD69+ and CD86+cells, while docetaxel at 30 mg/kg given on days 1 and 3 did not inhibit such activations (FIG. 24C).

Example 20

Figure 25:
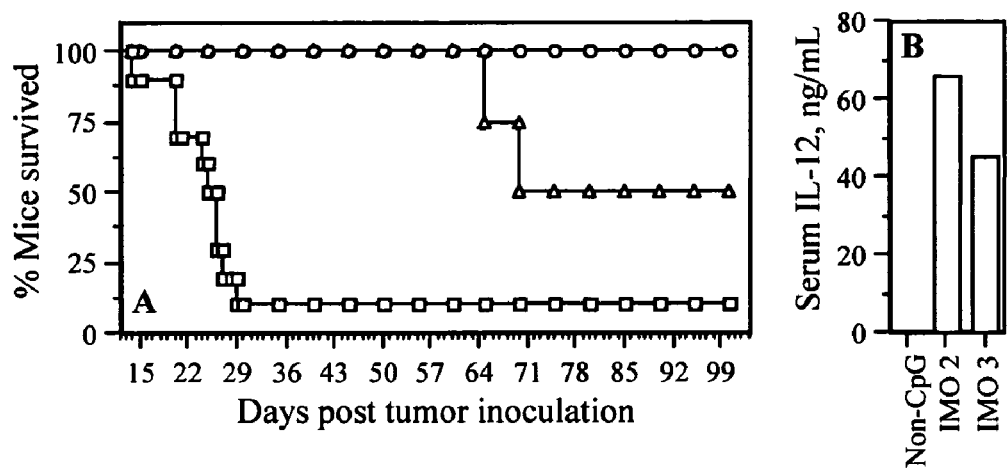
FIG. 25. (A) Antitumor effects of mouse and human IMOs 2 and 3, respectively, against CT26.CL25 colon tumor in BALB/c mice. IMO 2 (circles), IMO 3 (triangles) or non-CpG DNA (squares) (B) Serum IL-12 levels in mice 4 hr after administration of IMO motifs.
Figure 26:
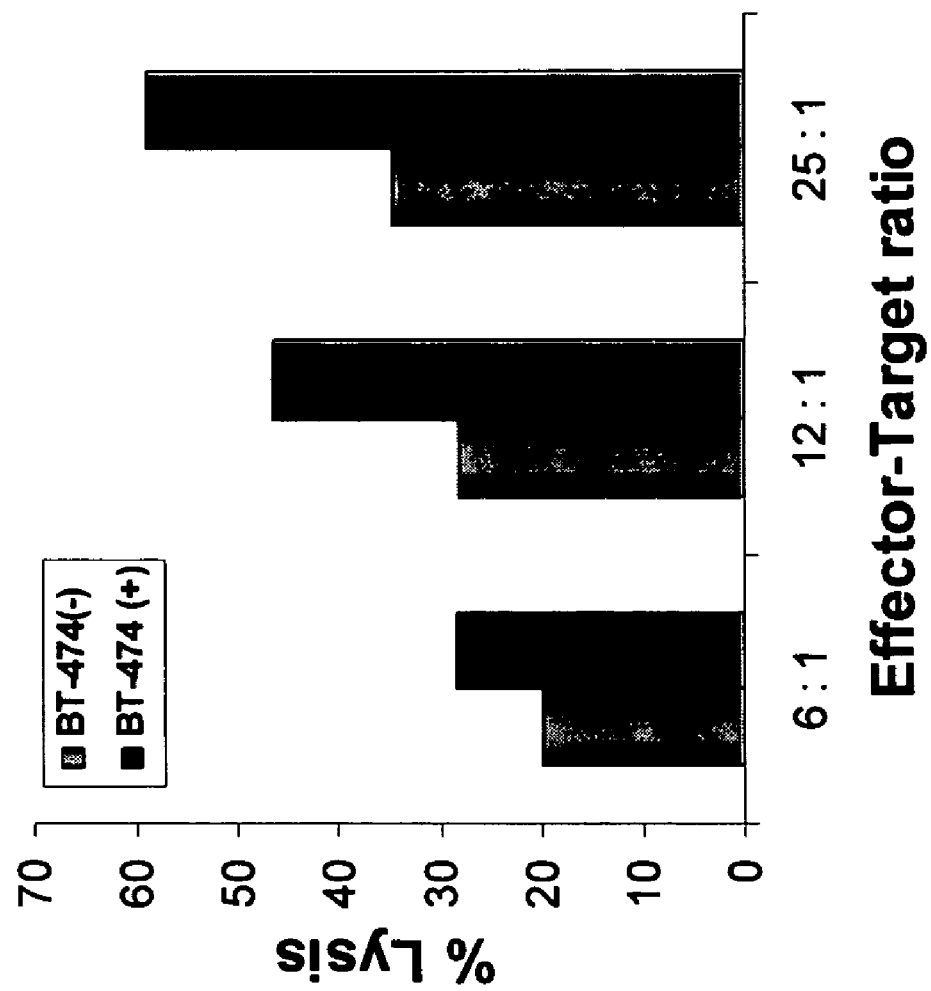
FIG. 26 shows IMO 3 activation of human PBMCs induce lysis of Her-2 positive BT-474 cells in the presence of Herceptin.

IMO 3 Containing Human-specific Motif Shows Potent Antitumor Activity and Induces Th-1 Cytokine, IL-12, in Tumor Bearing Mice Based on the results of IMO 2 that contained a mouse-specific immunostimulatory motif, IMO 3, which contained a human-specific motif, was synthesized and studied its activity against CT26.CL25 tumor in mice. IMO 3 also showed potent antitumor activity against this tumor model (FIG. 25A). As expected, both IMOs 2 and 3 induced IL-12 secretion in mice (FIG. 25B). Additionally, as shown in FIG. 26, activation of human PBMCs by IMO 3 induces lysis of Her-2 positive BT-474 cells in the presence of Herceptin.

Example 21

Enhanced Anti-tumor Effect of Rituxan in Combination with IMO Compounds

Figure 27:
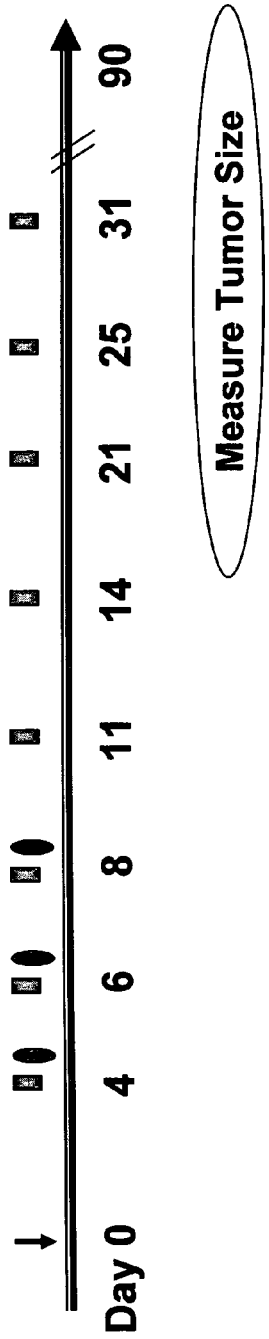
FIG. 27 shows the therapeutic schedule used in the Rituxan or Herceptin combination treatments with IMO compounds.
Figure 27:
Figure 28:
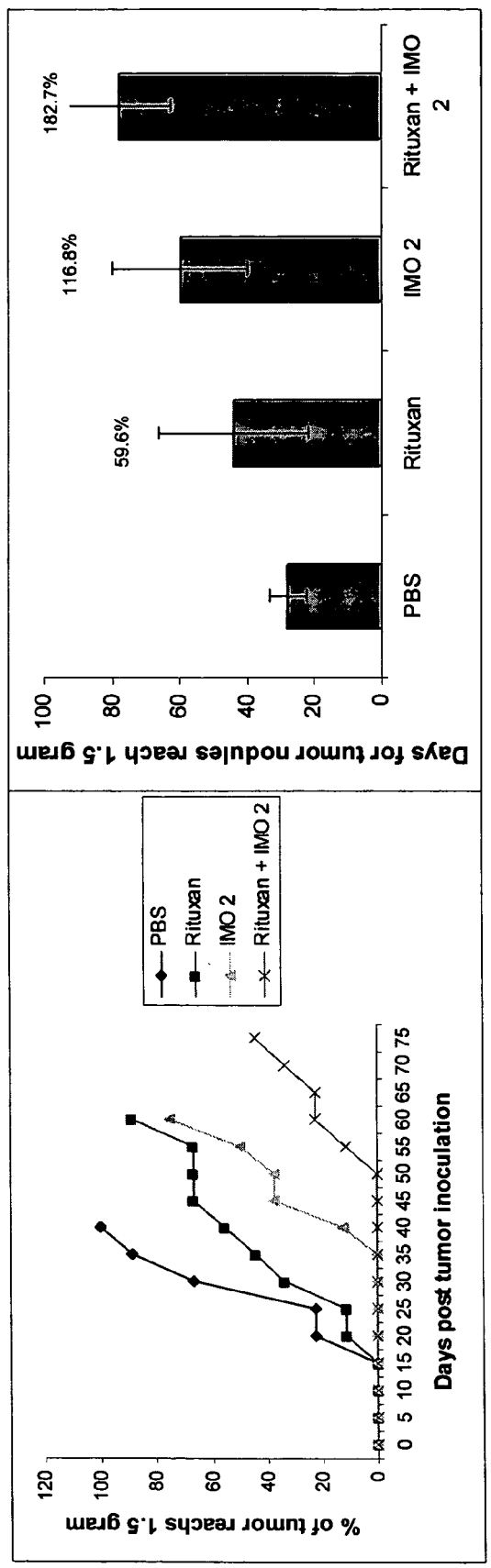
FIG. 28 shows the percentage of tumors and the number of days required for tumors to reach 1.5 grams with Rituxan and/or IMO treatment.

Namalwa B-cell lymphoma cells were implanted in NOD/SCID mice through intraperitoneal injection to generate a disease similar to human high-grade B-cell Non-Hodgkins Lymphoma. Tumor bearing mice were treated by intraperitoneal injections of 50 mg/kg Rituxan on days 4, 6 and 8 and/or 2.5 mg/kg IMO 2 on days 4, 6, 8, 11, 14 and 21 (FIG. 27). As shown in FIG. 28, tumor growth was significantly inhibited with the combination of Rituxan and IMO 2.

Example 22

IMO Compounds Potentiate Anti-tumor Effect of Herceptin

Figure 29:
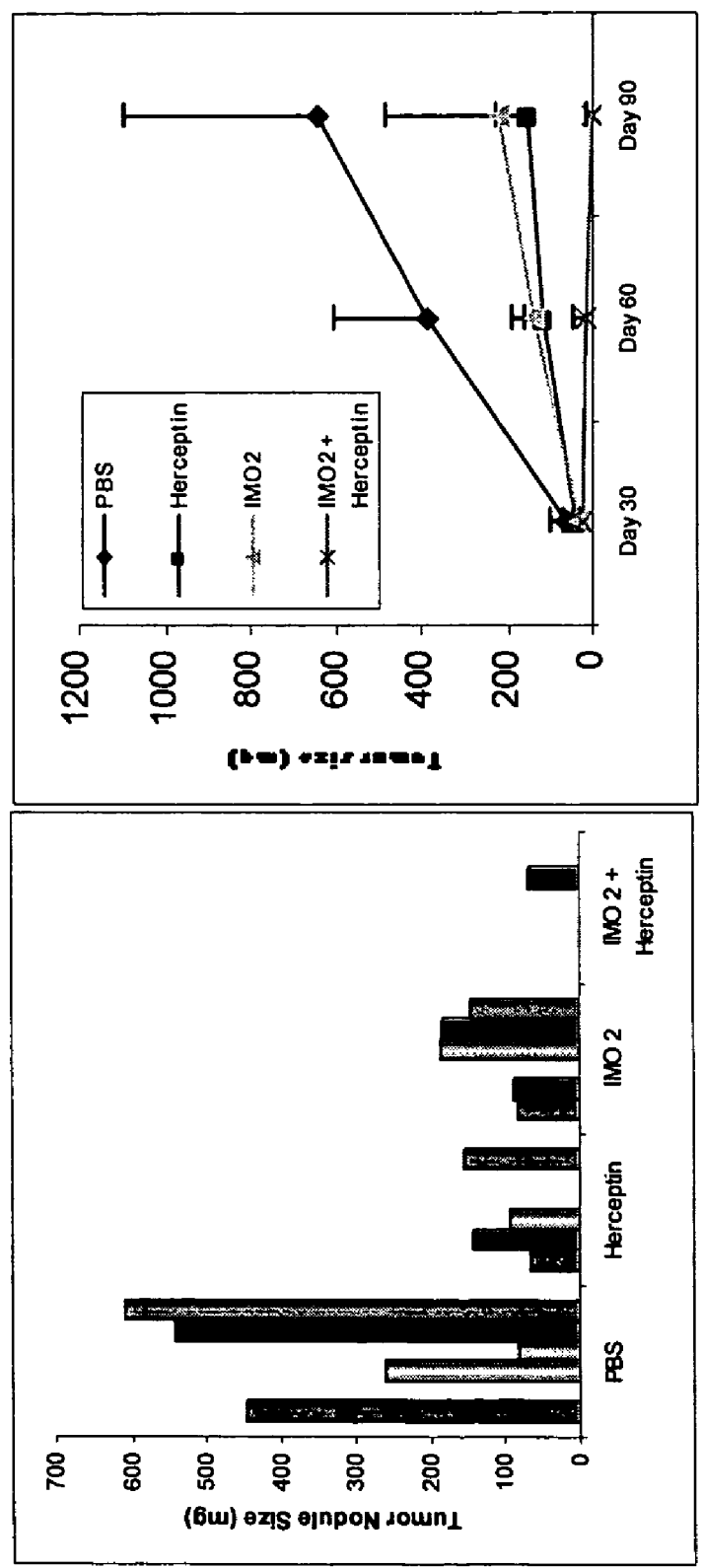
FIG. 29 shows the percent inhibition of tumor growth after Herceptin and/or IMO treatment.

Nude mice bearing subcutaneously implanted Her-2 overexpressing human breast tumors (BT474) were treated by intraperitoneal injection of 10 mg/kg Herceptin and/or peritumoral injection of 1 mg/kg IMO compound twice a week for 6 weeks (FIG. 27). Tumor growth after treatment with Herceptin or IMO 2 alone was inhibited 70% and 65% compared to the PBS control group (FIG. 29). A marked 97% suppression of tumor growth was found with combination treatment of Herceptin and IMO 2 (FIG. 29).

Example 23

IMO Compounds Potentiate Anti-tumor Effect of Herceptin

Figure 30:
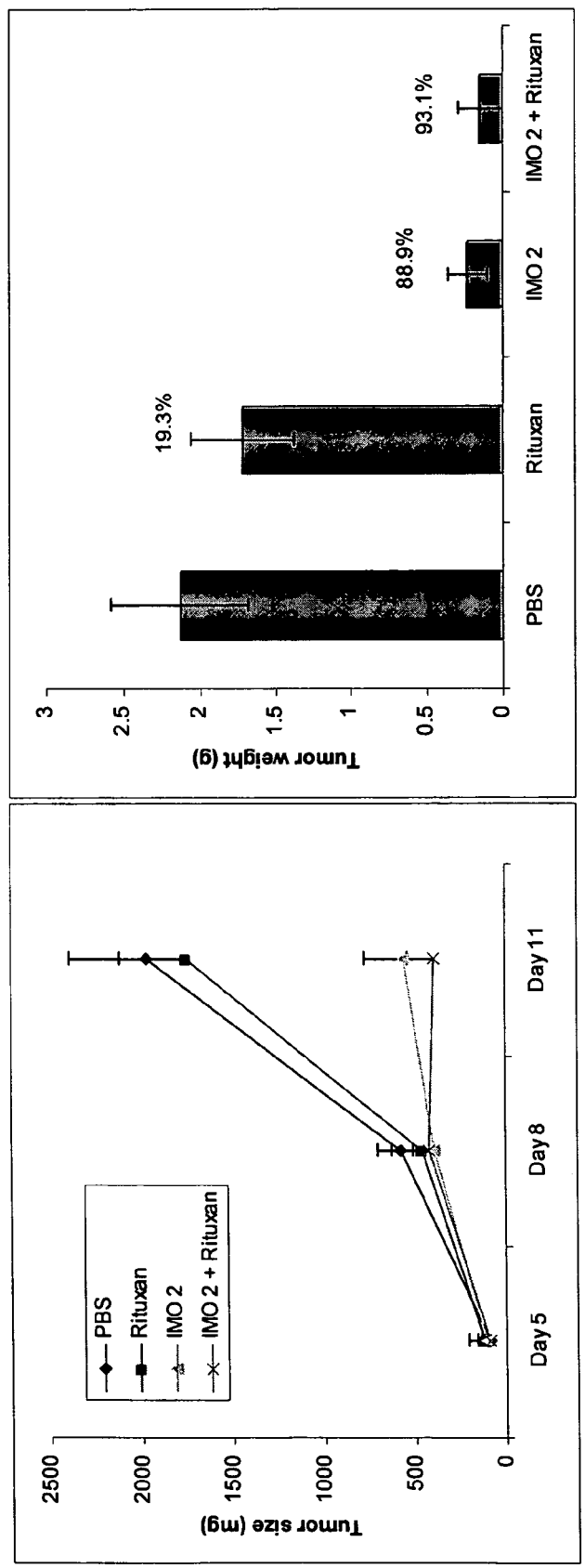
FIG. 30 shows the percent inhibition of tumor growth after Rituxan and/or IMO treatment.

Nude mice bearing subcutaneously implanted Her-2 overexpressing human breast tumors (BT474). Tumor bearing mice were treated by intraperitoneal injections of Rituxan on days 5, 7, 9 and 11 and/or IMO 2 on days 5, 7, 9, 11 and 13. As shown in FIG. 30, tumor growth was significantly inhibited with IMO 2 and the combination of Rituxan and IMO 2.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. A method for treating cancer comprising administering to a patient an immunomer in combination with a monoclonal antibody selected from Panorex® (edrecolomab), Rituxan® (rituximab), Mylotarg® (gemtuzumab ozogamicin), Campath® (alemtuzumab), Zevalin® (ibritumomab tiuxetan), Bexxar® (tositumomab), Erbitux® (cetuximab), Avastin® (bevacizumab or Herceptin® (trastuzumab), wherein the immunomer comprises the structure 5'-TCGTTGX-Y-XGT-TGCT-5' wherein X is a C3 linker and Y is a glycerol linker or comprises the structure (SEQ ID NO 18):

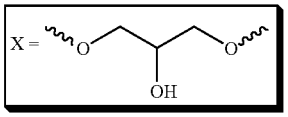

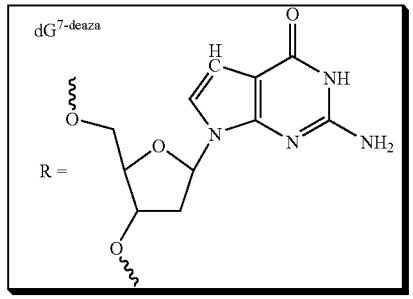

and wherein the anti-tumor effects of the monoclonal antibody are enhanced when administered in combination with the immunomer.

2. A pharmaceutical formulation comprising an immunomer, wherein the immunomer comprises the structure 5'-TCGTTGX-Y-XGTTGCT-5' wherein X is a C3 linker and Y is a glycerol linker or comprises the structure (SEQ ID NO 18):

5'-TCTGTCRTTCT-3'
                  \
                   X
                  /
5'-TCTGTCRTTCT-3'

X = [methoxy-glycerol-methoxy structure with OH]

dG$^{7\text{-}deaza}$ [structure]

R =

;

a monoclonal antibody selected from Panorex® (edrecolomab), Rituxan® (rituximab), Mylotarg® (gemtuzumab ozogamicin), Campath® (alemtuzumab), Zevalin® (ibritumomab tiuxetan), Bexxar® (tositumomab), Erbitux® (cetuximab), Avastin® bevacizumab or Herceptin® (trastuzumab) and a physiologically acceptable carrier.

* * * * *

UNITED STATES PATENT AND TRADEMARK OFFICE
CERTIFICATE OF CORRECTION

| | |
|---|---|
| PATENT NO. | : 7,569,554 B2 |
| APPLICATION NO. | : 10/846167 |
| DATED | : August 4, 2009 |
| INVENTOR(S) | : Ekambar R. Kandimalla et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,265 days.

Signed and Sealed this
Twenty-seventh Day of May, 2014

Michelle K. Lee
*Deputy Director of the United States Patent and Trademark Office*

```
                            SEQUENCE LISTING

<160> NUMBER OF SEQ ID NOS: 38

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagaacgctc gacctt                                                        16

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctatctgacg ttctctgt                                                      18

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgacgttctc tgt                                                           13

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (9)
<223> OTHER INFORMATION: 5OHdC

<400> SEQUENCE: 4
ctatctgang ttctctgt                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 5
ctatctgacn ttctctgt                                                   18

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 6
ctgangttct ctgt                                                       14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 7
ctgacnttct ctgt                                                       14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctgacgttct ctgt                                                       14

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (1)..(2)
<223> OTHER INFORMATION: 1',2'-dideoxyriboside

<400> SEQUENCE: 9
nntgacgttc tctgt                                                    15

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 10
nnntgacgtt ctctgt                                                   16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (7)
<223> OTHER INFORMATION: 5OHdC

<400> SEQUENCE: 11
nnntgangtt ctctgt                                                   16

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (8)
<223> OTHER INFORMATION: 7-deaza-dG

<400> SEQUENCE: 12
nnntgacntt ctctgt                                                   16

<210> SEQ ID NO 13
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
```
tctgacgttc t                                                           11

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 14
nnntctgacg ttct                                                        14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (9)
<223> OTHER INFORMATION: 5OHdC

<400> SEQUENCE: 15
nnntctgang ttct                                                        14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (10)
<223> OTHER INFORMATION: 7-deaza-dG

<400> SEQUENCE: 16
nnntctgacn ttct                                                        14

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ctatctgtcg ttctctgt                                                    18

<210> SEQ ID NO 18
<211> LENGTH: 11
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 18
tctgtcnttc t                                                             11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 19
tctgtcnttc t                                                             11

<210> SEQ ID NO 20
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 20
tctgtnnttc t                                                             11

<210> SEQ ID NO 21
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 21
nntctgtcnt tct                                                           13

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (6)
<223> OTHER INFORMATION: AraG

<400> SEQUENCE: 22
ctgtcnttct ctgt                                                         14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG

<400> SEQUENCE: 23
ctgtnnttct ctgt                                                         14

<210> SEQ ID NO 24
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 24
tctgacnttc t                                                            11

<210> SEQ ID NO 25
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 25
nntctgacnt tct                                                          13

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (7)
<223> OTHER INFORMATION: AraG

<400> SEQUENCE: 26
tctgacnttc t                                                                11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 27
tctgannttc t                                                                11

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC

<400> SEQUENCE: 28
ctgangttct ctgt                                                             14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 29
ctgacnttct ctgt                                                             14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG
```

```
<400> SEQUENCE: 30 ctganntict ctgt                                                    14

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ctcactttcg ttctctgt                                                18

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 32
tctttngttc t                                                       11

<210> SEQ ID NO 33
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 33
tctttcnttc t                                                       11

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 34
tctgtngttc t                                                       11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
```

```
-continued

<223> OTHER INFORMATION: 7-deaza-dG

<400> SEQUENCE: 35
tctgtcnttc t                                                    11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 36
tctgangttc t                                                    11

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ctgacgttct                                                      10

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ctatctcacc ttctctgt                                             18
```